US011937788B2

United States Patent
Iwane

(10) Patent No.: US 11,937,788 B2
(45) Date of Patent: Mar. 26, 2024

(54) ENDOSCOPE SYSTEM

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 597 days.

(21) Appl. No.: 17/171,802

(22) Filed: Feb. 9, 2021

(65) Prior Publication Data
US 2021/0161372 A1 Jun. 3, 2021

Related U.S. Application Data

(63) Continuation of application No. PCT/JP2019/031135, filed on Aug. 7, 2019.

(30) Foreign Application Priority Data

Aug. 20, 2018 (JP) .................................. 2018-154122

(51) Int. Cl.
*A61B 1/06* (2006.01)
*A61B 1/00* (2006.01)
(Continued)

(52) U.S. Cl.
CPC ...... *A61B 1/0638* (2013.01); *A61B 1/000094* (2022.02); *A61B 1/00045* (2013.01); *A61B 1/00057* (2013.01); *A61B 1/05* (2013.01); *A61B 1/0655* (2022.02); *A61B 1/0661* (2013.01); *A61B 1/2736* (2013.01)

(58) Field of Classification Search
CPC ............ A61B 1/0638; A61B 1/000094; A61B 1/00045; A61B 1/00057; A61B 1/05;
(Continued)

(56) References Cited

U.S. PATENT DOCUMENTS

2012/0116159 A1* 5/2012 Mizuyoshi ........... A61B 1/0653
600/109
2017/0231502 A1 8/2017 Nagaoka
(Continued)

FOREIGN PATENT DOCUMENTS

CN 102266217 A 12/2011
CN 102727162 A 10/2012
(Continued)

OTHER PUBLICATIONS

An Office Action; "Notice of Reasons for Refusal," mailed by the Japanese Patent Office dated Mar. 8, 2022, which corresponds to Japanese Patent Application No. 2020-538293 and is related to U.S. Appl. No. 11/171,802 with English language translation.
(Continued)

*Primary Examiner* — Michael E Teitelbaum
(74) *Attorney, Agent, or Firm* — Studebaker & Brackett PC

(57) ABSTRACT

First illumination light and second illumination light having different emission spectra are automatically switched so as to be emitted for a light emission period of at least one or more frames under specific light amount conditions, respectively. First image signals obtained in a case where an image is picked up using the first illumination light and second image signals obtained in a case where an image is picked up using the second illumination light are acquired. A first specific color signal for specific biological tissue among the first image signals and a second specific color signal for the specific biological tissue among the second image signals match.

14 Claims, 25 Drawing Sheets

(51) Int. Cl.
*A61B 1/05* (2006.01)
*A61B 1/273* (2006.01)

(58) Field of Classification Search
CPC ... A61B 1/0655; A61B 1/0661; A61B 1/2736; A61B 1/00006; A61B 1/045; G02B 23/24; G02B 23/26
See application file for complete search history.

(56) References Cited

U.S. PATENT DOCUMENTS

| | | | |
|---|---|---|---|
| 2019/0117055 A1* | 4/2019 | Ito | ........................ G02B 23/2461 |
| 2019/0222737 A1 | 7/2019 | Aoyama | |

FOREIGN PATENT DOCUMENTS

| | | |
|---|---|---|
| JP | 2015173737 A | 10/2015 |
| JP | 2016077756 A | 5/2016 |
| JP | 2017185258 A | 10/2017 |
| WO | 2016080130 A1 | 5/2016 |
| WO | 2017/216883 A1 | 12/2017 |
| WO | 2018/066347 A1 | 4/2018 |

OTHER PUBLICATIONS

International Search Report issued in PCT/JP2019/031135; dated Nov. 12, 2019.

International Preliminary Report on Patentability and Written Opinion issued in PCT/JP2019/031135; dated Feb. 23, 2021.

An Office Action; "Decision of Refusal", mailed by the Japanese Patent Office dated Jun. 14, 2022, which corresponds to Japanese Patent Application No. 2020-538293 and is related to U.S. Appl. No. 17/171,802 with English language translation.

An Office Action mailed by China National Intellectual Property Administration dated Oct. 21, 2023, which corresponds to Chinese Patent Application No. 201980054736.8 and is related to U.S. Appl. No. 17/171,802; with English translation.

* cited by examiner

ENDOSCOPE SYSTEM

CROSS-REFERENCE TO RELATED APPLICATIONS

This application is a Continuation of PCT International Application No. PCT/JP2019/031135 filed on 7 Aug. 2019, which claims priority under 35 U.S.C. § 119(a) to Japanese Patent Application No. 2018-154122 filed on 20 Aug. 2018. The above application is hereby expressly incorporated by reference, in its entirety, into the present application.

BACKGROUND OF THE INVENTION

1. Field of the Invention

The present invention relates to an endoscope system that switches and displays a plurality of kinds of images.

2. Description of the Related Art

In recent years, an endoscope system comprising a light source device, an endoscope, and a processor device has been widely used in a medical field. In the endoscope system, an object to be observed is irradiated with illumination light from an endoscope, and the image of the object to be observed is displayed on a monitor on the basis of RGB image signals that are obtained in a case where the image of the object to be observed, which is being illuminated with the illumination light, is picked up by an image pickup element of the endoscope.

In recent years, an object to be observed has been illuminated with a plurality of kinds of illumination light having wavelength ranges different from each other according to the purpose of diagnosis. For example, JP2015-173737A discloses that an object to be observed is alternately illuminated with two kinds of blue narrow-band light, that is, NB1 light having a peak wavelength of 422 nm and NB2 light having a peak wavelength in the range of 460 to 470 nm to acquire oxygen saturation in blood vessels included in the object to be observed. Further, WO2016/080130A (corresponding to US2017/0231502A1) discloses that an object to be observed is illuminated with light having a peak in a B1 region (first B region: 390 nm to 440 nm) and light having a peak in a B2 region (second B region: 440 nm to 490 nm) and the image of the object to be observed is picked up by an image pickup element including B-pixels having sensitivity to both light of the B1 region and light of the B2 region to obtain image information about superficial blood vessels. Furthermore, JP2017-185258A discloses that desired tissue information about biological tissue is acquired as more clear information suitable for diagnosis using violet light having a central wavelength of 405 nm, blue laser light having a central wavelength of 445 nm, and the excitation emission of light excited and emitted by blue laser light.

SUMMARY OF THE INVENTION

In recent years, a diagnosis focusing on information other than a background mucous membrane, for example, blood vessels having different depths, glandular structures having different depths or heights, or the like has been made in an endoscopic field. A plurality of kinds of information other than the background mucous membrane need to be displayed in such a diagnosis so that a user can grasp the information. A method including automatically switching various kinds of light and illuminating an object with the various kinds of light, which have different invasion depths to biological tissue and a plurality of wavelengths, and switching and displaying a plurality of images obtained from the illumination is considered as a method of displaying each of the plurality of kinds of information. For example, in order to obtain information about a surface layer, such as superficial blood vessels, and information about an intermediate layer, such as intermediate blood vessels, a user illuminates an object with short-wavelength light having an invasion depth to a surface layer and medium-wavelength light having an invasion depth to an intermediate layer while switching the short-wavelength light and the medium-wavelength light, and switches and displays a surface layer image obtained from illumination using the short-wavelength light and an intermediate layer image obtained from illumination using the medium-wavelength light. Since a difference between the surface layer image and the intermediate layer image is displayed in a case where such switching display is performed, the user can grasp information about the surface layer and information about the intermediate layer.

However, in a case where a user illuminates an object with the short-wavelength light and the medium-wavelength light while switching the short-wavelength light and the medium-wavelength light, the tint of the entire surface layer image and the tint of the entire intermediate layer image are significantly different from each other in a case where the signal value of the surface layer image and the signal value of the intermediate layer image are significantly different from each other. Since a difference in the tint of the entire image is also displayed in this case, the visibility of information about the surface layer and information about the intermediate layer to which a user pays attention at the time of diagnosis deteriorates. As a method of correcting a difference in the tint of the entire image, there is a method of causing the tint of a surface layer image and the tint of an intermediate layer image to match using image processing, such as white balance processing. However, since a difference in a gain factor used for tint matching is generated in white balance processing even though the tint of a surface layer image and the tint of an intermediate layer image match, a difference in noise is generated between the images.

An object of the invention is to provide an endoscope system that can visualize a difference between images while causing the tints of the respective images to match in a case where an object is illuminated with a plurality of kinds of light while the plurality of kinds of light are switched and a plurality of images obtained from illumination using the respective kinds of light are switched and displayed.

An endoscope system according to an aspect of the invention comprises a light source unit, a light source controller, an image pickup sensor, and an image acquisition unit. The light source unit emits first illumination light and second illumination light having an emission spectrum different from an emission spectrum of the first illumination light. The light source controller automatically switches the first illumination light and the second illumination light and emits each of the first illumination light and the second illumination light for a light emission period of at least one or more frames. The image pickup sensor includes specific pixels having sensitivity to the first illumination light and the second illumination light. The image acquisition unit acquires first image signals obtained in a case where an image of biological tissue illuminated with the first illumination light is picked up by the image pickup sensor, and second image signals obtained in a case where an image of biological tissue illuminated with the second illumination light is picked up by the image pickup sensor. In the endoscope system according to the aspect of the invention, the first image signals include first specific color signals output from the specific pixels, the second image signals include second specific color signals output from the specific pixels, and the light source controller causes the first illumination light and the second illumination light to be emitted under specific light amount conditions, so that a signal value of the first specific color signal for specific biological tissue corresponding to at least specific biological tissue, which is a part of the biological tissue, among the first specific color signals is equal to a signal value of the second specific color signal for specific biological tissue corresponding to at least the specific biological tissue among the second specific color signals.

It is preferable that a light amount condition of the first illumination light and a light amount condition of the second illumination light in a case where a first calculation value obtained using a light intensity of the first illumination light, a spectral reflectivity of the specific biological tissue, and a spectral sensitivity of the specific pixel is equal to a second calculation value obtained using a light intensity of the second illumination light, the spectral reflectivity of the specific biological tissue, and the spectral sensitivity of the specific pixel are used as the specific light amount conditions.

It is preferable that the spectral reflectivity of the specific biological tissue is an average spectral reflectivity of a plurality of parts obtained by averaging of spectral reflectivities of biological tissue of the plurality of parts. It is preferable that the plurality of parts include a gullet, a stomach, and a large intestine. It is preferable that the spectral reflectivity of the specific biological tissue is a spectral reflectivity of a background mucous membrane. It is preferable that the spectral reflectivity of the specific biological tissue is an average spectral reflectivity of the entire biological tissue. It is preferable that the spectral reflectivity of the specific biological tissue is any one of a spectral reflectivity of a high-oxygen portion including a specific percentage or higher of oxyhemoglobin or a spectral reflectivity of a low-oxygen portion including a specific percentage or higher of reduced hemoglobin.

It is preferable that the endoscope system according to the aspect of the invention further comprises a calibration signal acquisition unit and a light amount condition-calculation unit. The calibration signal acquisition unit acquires image signals for first calibration obtained in a case where an image of the specific biological tissue illuminated with different light of the first illumination light and the second illumination light is picked up by the image pickup sensor and image signals for second calibration obtained in a case where an image of the specific biological tissue illuminated with common light of the first illumination light and the second illumination light is picked up by the image pickup sensor. The light amount condition-calculation unit calculates the specific light amount conditions using a specific color signal for first calibration output from the specific pixel among the image signals for first calibration and a specific color signal for second calibration output from the specific pixel among the image signals for second calibration.

It is preferable that the first illumination light includes violet light, green light, and red light, the second illumination light includes blue light, green light, and red light, light intensity ratios of the green light and the red light included in the first illumination light are equal to light intensity ratios of the green light and the red light included in the second illumination light, and the specific pixel is a blue pixel having sensitivity to the violet light and the blue light.

It is preferable that the first illumination light includes violet light, blue light, green light, and red light, a light intensity ratio of the violet light included in the first illumination light is higher than a light intensity ratio of the blue light included in the first illumination light, the second illumination light includes violet light, blue light, green light, and red light, a light intensity ratio of the blue light included in the second illumination light is higher than a light intensity ratio of the violet light included in the second illumination light, light intensity ratios of the green light and the red light included in the first illumination light are equal to light intensity ratios of the green light and the red light included in the second illumination light, the light intensity ratio of the violet light included in the first illumination light is different from the light intensity ratio of the violet light included in the second illumination light, the light intensity ratio of the blue light included in the first illumination light is different from the light intensity ratio of the blue light included in the second illumination light, and the specific pixel is a blue pixel having sensitivity to the violet light and the blue light. It is preferable that the first illumination light includes first red narrow-band light and the second illumination light includes second red narrow-band light of which a wavelength is different from a wavelength of the first red narrow-band light and the specific pixel is a red pixel having sensitivity to the first red narrow-band light and the second red narrow-band light.

It is preferable that the endoscope system further comprises a display controller causing a display unit to automatically switch and display a first observation image obtained on the basis of the first image signals and a second observation image obtained on the basis of the second image signals.

According to the invention, it is possible to visualize a difference between images while causing the tints of the respective images to match in a case where an object is illuminated with a plurality of kinds of light while the plurality of kinds of light are switched and a plurality of images obtained from illumination using the respective kinds of light are switched and displayed.

DESCRIPTION OF THE PREFERRED EMBODIMENTS

First Embodiment

Figure 1:
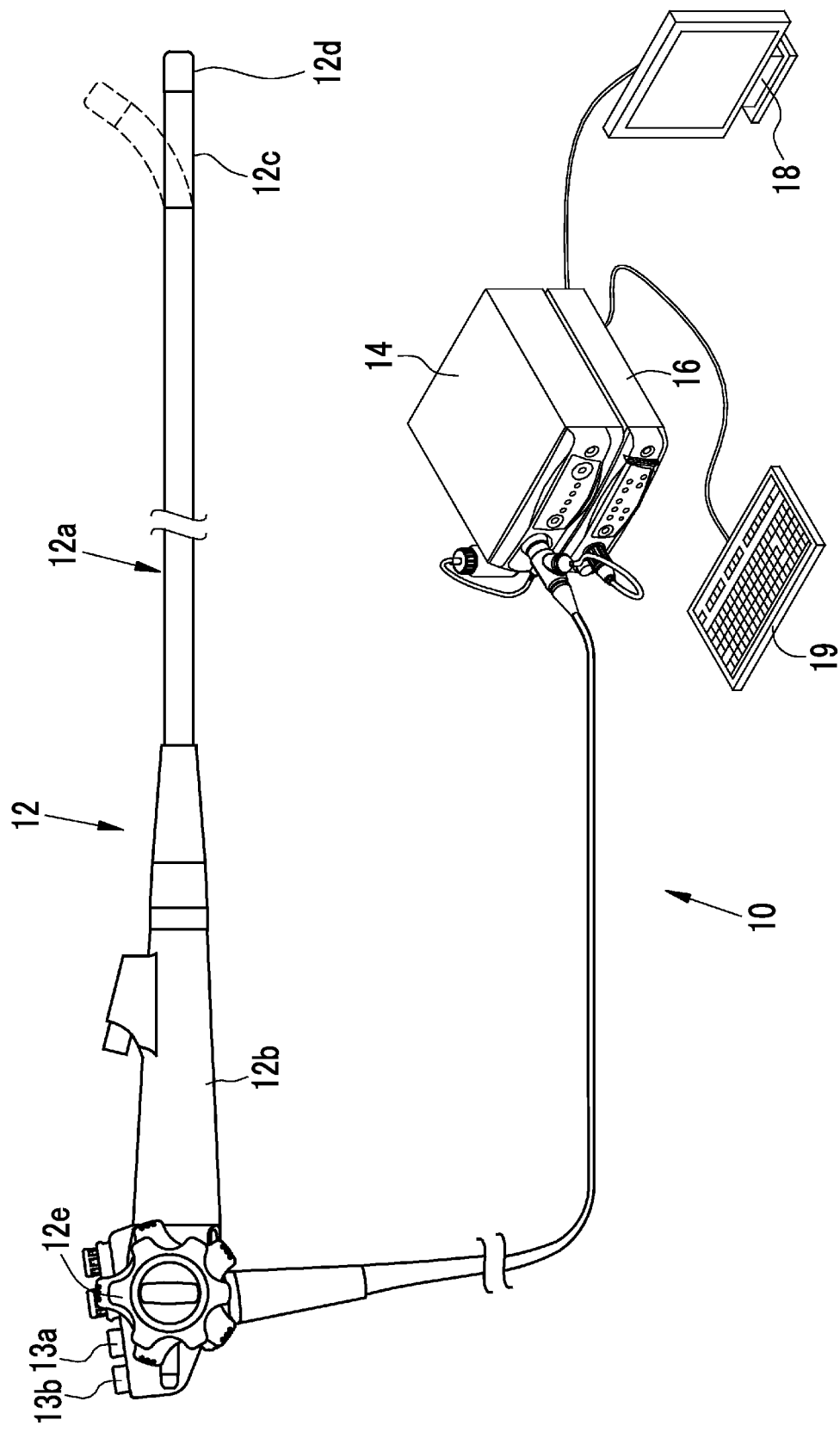
FIG. 1 is a diagram showing the appearance of an endoscope system according to a first embodiment.

As shown in FIG. 1, an endoscope system 10 according to a first embodiment includes an endoscope 12, a light source device 14, a processor device 16, a monitor 18 (display unit), and a user interface 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d faces in a desired direction. The user interface 19 includes a mouse and the like in addition to a keyboard shown in FIG. 1.

Further, the operation part 12b is provided with a mode changeover SW 13a and a static image-acquisition instruction unit 13b in addition to the angle knobs 12e. The mode changeover SW 13a is used for an operation for switching a normal observation mode, a first special observation mode, a second special observation mode, and a multi-observation mode. The normal observation mode is a mode where a normal image is displayed on the monitor 18. The first special observation mode is a mode where a first special observation image in which surface layer information, such as superficial blood vessels, are emphasized is displayed on the monitor 18. The second special observation mode is a mode where a second special observation image in which intermediate layer information, such as intermediate blood vessels, are emphasized is displayed on the monitor 18. The multi-observation mode is a mode where the first special observation image (first observation image) and the second special observation image (second observation image) are automatically switched and displayed on the monitor 18. A foot switch may be used as a mode switching unit, which is used to switch a mode, other than the mode changeover SW 13a.

The processor device 16 is electrically connected to the monitor 18 and the user interface 19. The monitor 18 outputs and displays image information and the like. The user interface 19 functions as a user interface (UI) that receives an input operation, such as function settings. An external recording unit (not shown), which records image information and the like, may be connected to the processor device 16.

Figure 2:
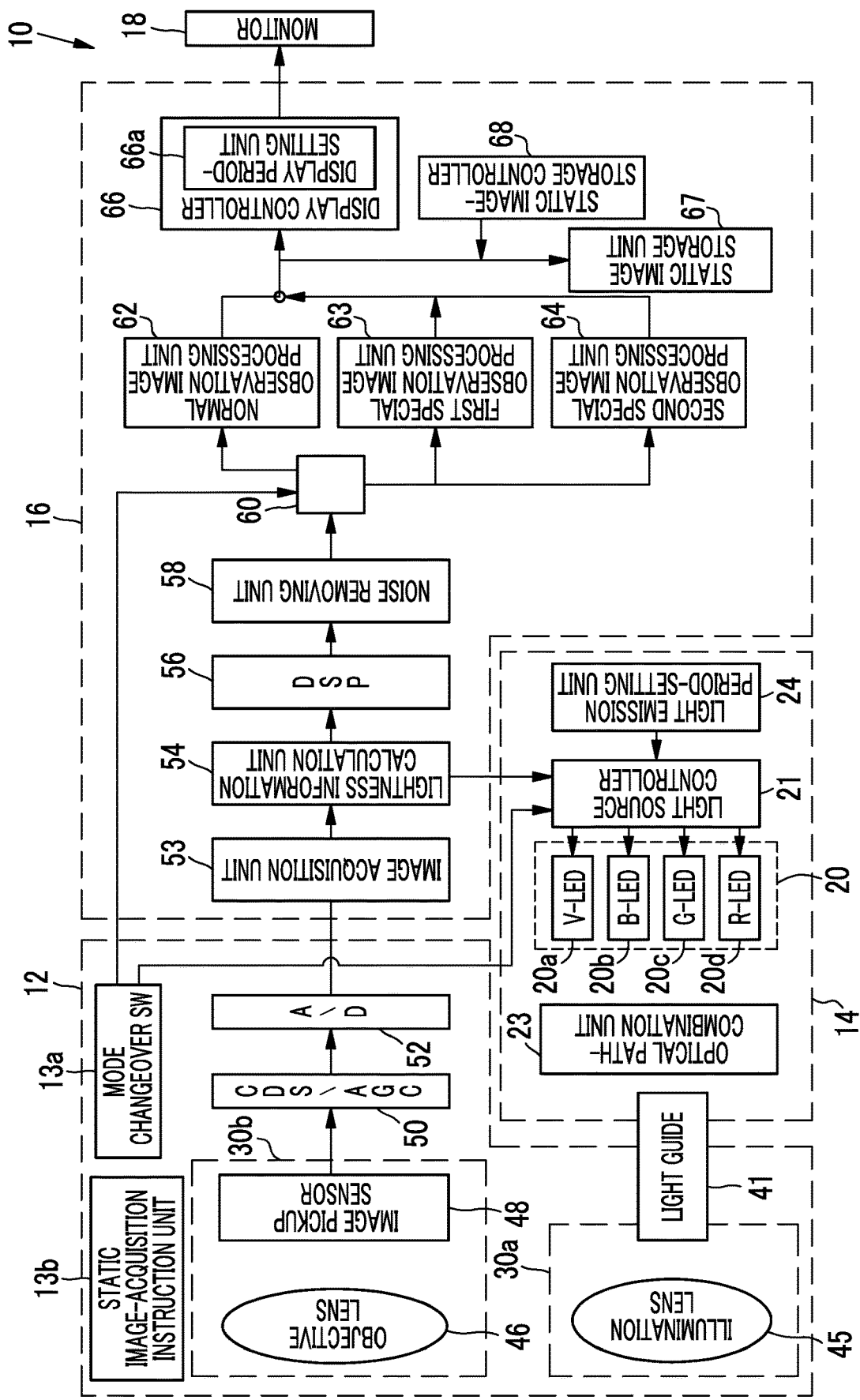
FIG. 2 is a block diagram showing the functions of the endoscope system according to the first embodiment.

As shown in FIG. 2, the light source device 14 includes a light source unit 20, a light source controller 21, and an optical path-combination unit 23. The light source unit 20 includes a violet light emitting diode (V-LED) 20a, a blue light emitting diode (B-LED) 20b, a green light emitting diode (G-LED) 20c, and a red light emitting diode (R-LED) 20d. The light source controller 21 controls the drive of the LEDs 20a to 20d. The optical path-combination unit 23 combines the optical paths of four kinds of color light that are emitted from the four color LEDs 20a to 20d. The inside of an object to be examined is irradiated with the pieces of light, which are combined by the optical path-combination unit 23, through a light guide 41 inserted into the insertion part 12a and an illumination lens 45. A laser diode (LD) may be used instead of the LED.

Figure 3:
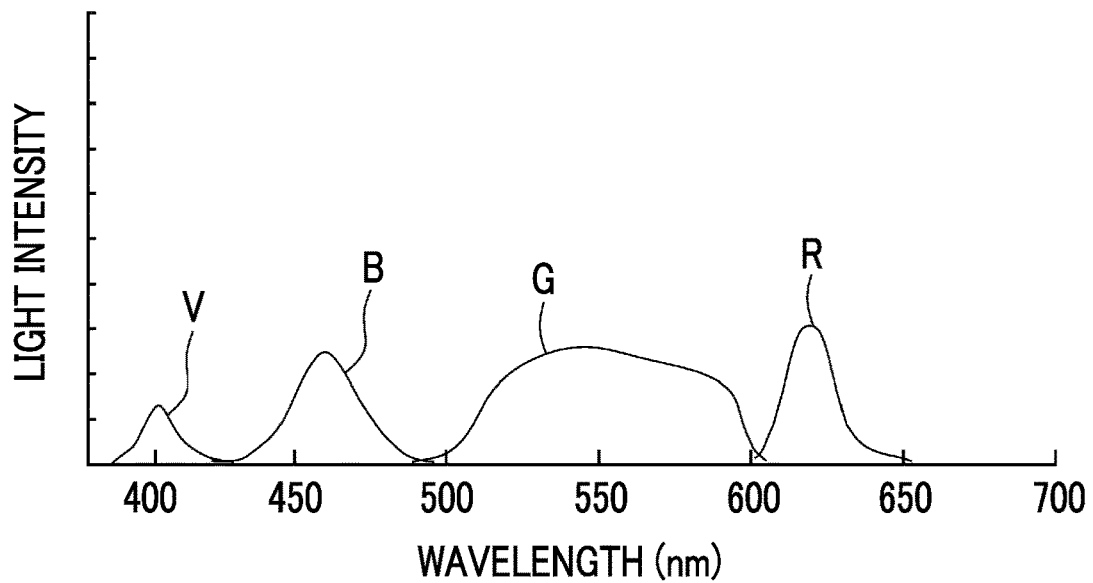
FIG. 3 is a graph showing the emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

The light source controller 21 controls the V-LED 20a, the B-LED 20b, the G-LED 20c, and the R-LED 20d. Further, the light source controller 21 controls the respective LEDs 20a to 20d so that normal light of which the light intensity ratios of violet light V, blue light B, green light G, and red light R are Vc:Bc:Gc:Rc is emitted in the normal observation mode.

Figure 4:
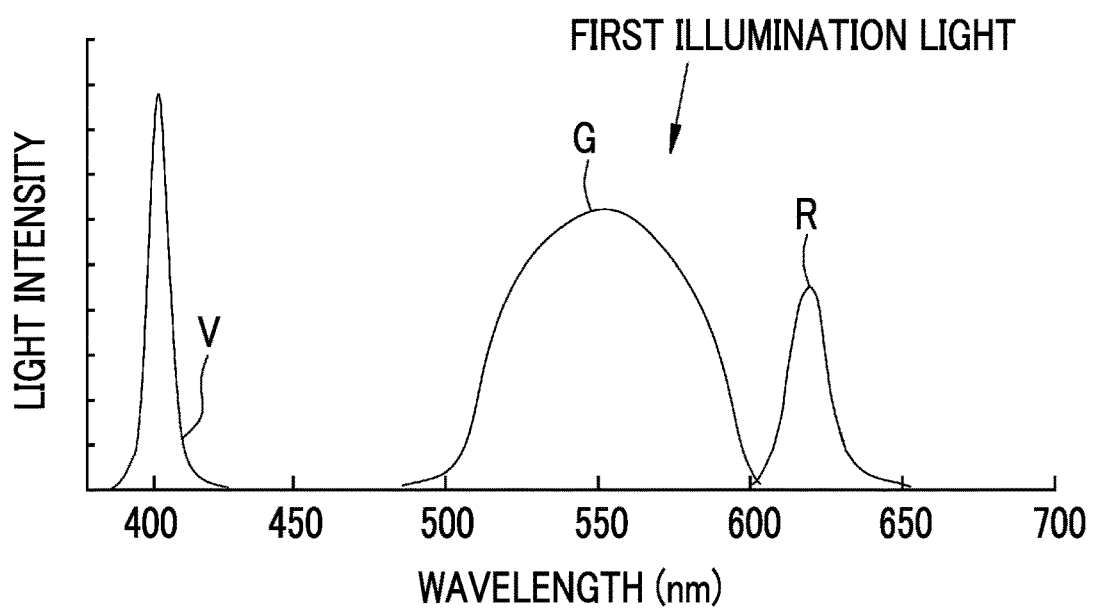
FIG. 4 is a graph showing the emission spectrum of first illumination light that includes violet light V, green light G, and red light R.

Furthermore, the light source controller 21 controls the respective LEDs 20a to 20d so that first illumination light of which the light intensity ratios of violet light V, blue light B, green light G, and red light R are Vs1:Bs1:Gs1:Rs1 is emitted in the first special observation mode. The light intensity ratios Vs1:Bs1:Gs1:Rs1 correspond to the light amount condition of the first illumination light. It is preferable that the first illumination light can emphasize superficial blood vessels and accurately reproduce the color of a background mucous membrane. For this purpose, it is preferable that, for example, Bs1 is set to "0" and Vs1, Gs1, and Rs1 are set to be larger than "0" as shown in FIG. 4. Since the first illumination light in this case includes violet light, green light, and red light, the first illumination light can emphasize the above-mentioned superficial blood vessels, accurately reproduce the color of a background mucous membrane, and also emphasize various structures, such as glandular structures and unevenness.

In this specification, the light intensity ratios include a case where the ratio of at least one semiconductor light source is 0 (zero). Accordingly, the light intensity ratios include a case where any one or two or more of the respective semiconductor light sources are not turned on. For example, even though only one semiconductor light source is turned on and the other three semiconductor light sources are not turned on as in a case where the light intensity ratios of violet light V, blue light B, green light G, and red light R are 1:0:0:0, it is regarded that the light source unit 20 has light intensity ratios.

Figure 5:
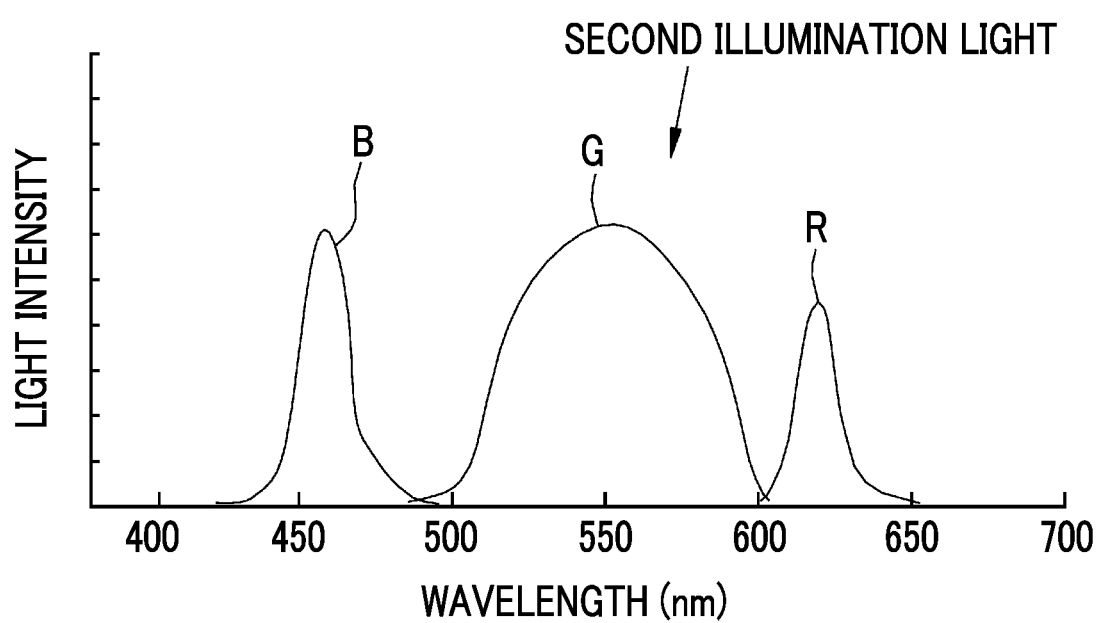
FIG. 5 is a graph showing the emission spectrum of second illumination light that includes blue light B, green light G, and red light R.

Further, the light source controller 21 controls the respective LEDs 20a to 20d so that second illumination light of which the light intensity ratios of violet light V, blue light B, green light G, and red light R are Vs2:Bs2:Gs2:Rs2 is emitted in the second special observation mode. The light intensity ratios Vs2:Bs2:Gs2:Rs2 correspond to the light amount condition of the second illumination light. It is preferable that the second illumination light can emphasize intermediate blood vessels and accurately reproduce the color of a background mucous membrane. For this purpose, it is preferable that, for example, Vs2 is set to "0" and Bs2, Gs2, and Rs2 are set to be larger than "0" as shown in FIG. 5. Since the second illumination light in this case includes blue light, green light, and red light, the second illumination light can emphasize intermediate blood vessels and accurately reproduce the color of a background mucous membrane.

In a case where a mode is set to the multi-observation mode, the light source controller 21 performs control to emit each of the first illumination light and the second illumination light for a light emission period of one or more frames and to automatically switch and emit the first illumination light and the second illumination light. Further, the light source controller 21 controls the light source unit 20 so that the light amount condition of the first illumination light and the light amount condition of the second illumination light are set to specific light amount conditions and light is emitted. Since the first illumination light and the second illumination light are emitted under the specific light amount conditions, the signal value of a first blue color signal for specific biological tissue corresponding to at least specific biological tissue, which is a part of biological tissue, among first blue color signals (first specific color signals) included in the first special observation image is equal to the signal value of a second blue color signal for specific biological tissue corresponding to at least the specific biological tissue among second blue color signals (second specific color signals) included in the second special observation image. Under the specific light amount conditions, the light intensity ratio (Gs1:Rs1) of green light G and red light R included in the first illumination light and the light intensity ratio (Gs2:Rs2) of green light G and red light R included in the second illumination light are set to be equal to each other.

Accordingly, the tints of the background mucous membranes of the first and second special observation images match. Here, a case where the signal value of the first blue color signal for specific biological tissue and the signal value of the second blue color signal for specific biological tissue are equal to each other also includes a case where a difference between the signal value of the first blue color signal for specific biological tissue and the signal value of the second blue color signal for specific biological tissue is in a certain allowable range even though the signal value of the first blue color signal for specific biological tissue and the signal value of the second blue color signal for specific biological tissue are different from each other, in addition to a case where the signal values are completely equal to each other. The details of a method of setting the specific light amount conditions will be described later. The background mucous membrane means a region of an object to be observed not including regions that are to be recognized or subjected to image pickup as structures, such as blood vessels or glandular structures.

Figure 6:
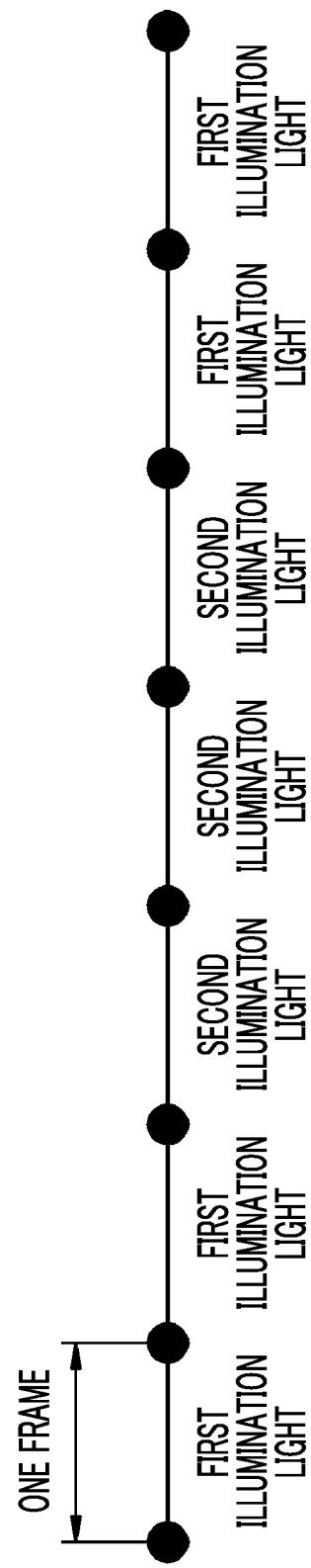
FIG. 6 is a diagram illustrating the light emission period of the first illumination light and the light emission period of the second illumination light.

Moreover, the light source controller 21 controls the amount of illumination light to be emitted from each of the LEDs 20a to 20d on the basis of lightness information sent from a lightness information calculation unit 54 of the processor device 16. Further, for example, in a case where the light source controller 21 sets the light emission period of the first illumination light to two frames and sets the light emission period of the second illumination light to three frames, the second illumination light continues to be emitted for three frames after the first illumination light continues to be emitted for two frames as shown in FIG. 6.

"Frame" means a unit used to control an image pickup sensor 48 that picks up the image of an object to be observed. For example, "one frame" means a period including at least an exposure period where the image pickup sensor 48 is exposed to light emitted from an object to be observed and a read-out period where image signals are read out. In this embodiment, the light emission period is determined so as to correspond to "frame" that is a unit of image pickup.

Figure 7:
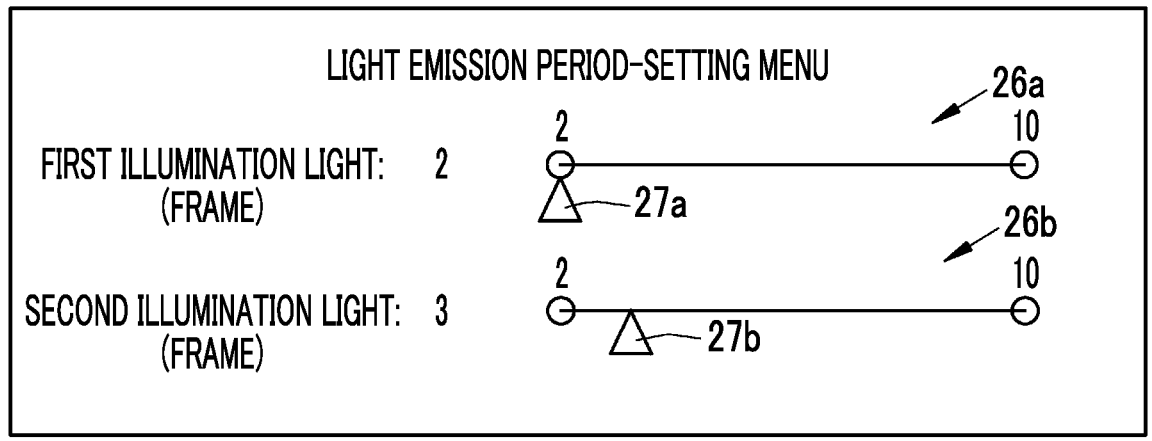
FIG. 7 is a diagram illustrating a light emission period-setting menu.

The light emission period of the first illumination light and the light emission period of the second illumination light can be appropriately changed by a light emission period-setting unit 24 that is connected to the light source controller 21. In a case where an operation for changing a light emission period is received by the operation of the user interface 19, the light emission period-setting unit 24 displays a light emission period-setting menu shown in FIG. 7 on the monitor 18. The light emission period of the first illumination light can be changed between, for example, two frames and ten frames. Each light emission period is assigned to a slide bar 26a.

In a case where the light emission period of the first illumination light is to be changed, a user operates the user interface 19 to position a slider 27a at a position on the slide bar 26a that represents a light emission period to which the user wants to change a light emission period. Accordingly, the light emission period of the first illumination light is changed. Even in the case of the light emission period of the second illumination light, a user operates the user interface 19 to position a slider 27b at a position on a slide bar 26b (to which a light emission period in the range of, for example, two frames to ten frames is assigned) that represents a light emission period to which the user wants to change a light emission period. Accordingly, the light emission period of the second illumination light is changed.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 μm, a cladding diameter of 125 μm, and a protective layer forming a covering is in the range of φ0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the invention is a color image pickup sensor used to obtain RGB image signals corresponding to three colors of R (red), G (green), and B (blue), that is, a so-called RGB image pickup sensor that comprises R-pixels (specific pixels) provided with R-filters, G-pixels provided with G-filters, and B-pixels (specific pixels) provided with B-filters.

Figure 8:
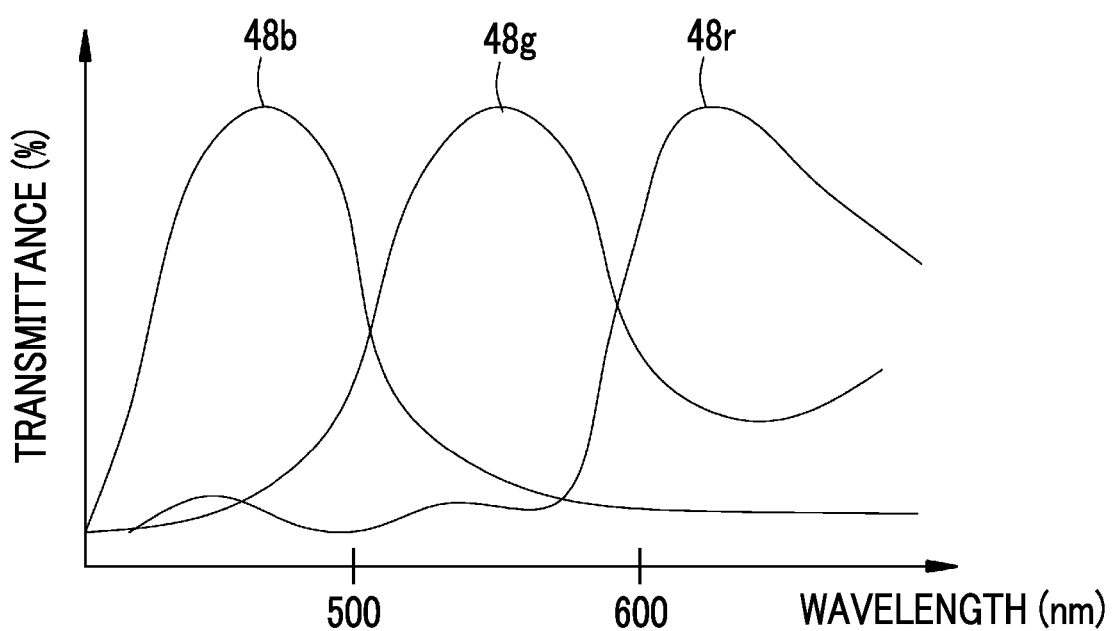
FIG. 8 shows the spectral transmittance of a B-filter, a G-filter, and an R-filter provided in an image pickup sensor.

As shown in FIG. 8, the B-filter 48b transmits light of a violet-light wavelength range, light of a blue-light wavelength range, and short-wavelength light of light of a green-light wavelength range. The G-filter 48g transmits light of a green-light wavelength range, long-wavelength light of light of a blue-light wavelength range, and short-wavelength light of light of a red-light wavelength range. The R-filter 48r transmits light of a red-light wavelength range and short-wavelength light of light of a green-light wavelength range. Accordingly, in the image pickup sensor 48, the B-pixel has sensitivity to violet light V, blue light B, and green light G, the G-pixel has sensitivity to blue light B, green light G, and red light R, and the R-pixel has sensitivity to green light G and red light R.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source controller 21 causes blue light B, green light G, and red light R to be emitted in a time-sharing manner, demosaicing needs to be added to processing for image pickup signals.

As shown in FIG. 2, the image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 52. The digital image signals, which have been subjected to A/D conversion, are input to the processor device 16.

The processor device 16 comprises an image acquisition unit 53, a lightness information calculation unit 54, a digital signal processor (DSP) 56, a noise removing unit 58, a signal switching unit 60, a normal observation image processing unit 62, a first special observation image processing unit 63, a second special observation image processing unit 64, a display controller 66, a static image storage unit 67, and a static image-storage controller 68.

The image acquisition unit 53 acquires an observation image that is obtained in a case where the image of the object to be observed is picked up in the endoscope 12. Specifically, digital color image signals obtained from the endoscope 12 are input to the image acquisition unit 53 as an observation image. The color image signals are formed of red color signals output from the R-pixels of the image pickup sensor 48, green color signals output from the G-pixels of the image pickup sensor 48, and blue color signals output from the B-pixels of the image pickup sensor 48. The lightness information calculation unit 54 calculates lightness information, which represents the lightness of the object to be observed, on the basis of the image signals input from the image acquisition unit 53. The calculated lightness information is sent to the light source controller 21 and is used for the control of the amount of illumination light to be emitted.

The DSP 56 performs various kinds of signal processing, such as defect correction processing, offset processing, gain correction processing, linear matrix processing, gamma conversion processing, and demosaicing processing, on the received image signals. Signals of defective pixels of the image pickup sensor 48 are corrected in the defect correction processing. Dark current components are removed from the image signals having been subjected to the defect correction processing in the offset processing, so that an accurate zero level is set. The image signals having been subjected to the offset processing are multiplied by a specific gain in the gain correction processing, so that signal levels are adjusted. The linear matrix processing for improving color reproducibility is performed on the image signals having been subjected to the gain correction processing. After that, lightness or a saturation is adjusted by the gamma conversion processing. The demosaicing processing (also referred to as equalization processing or demosaicing) is performed on the image signals having been subjected to the linear matrix processing, so that signals of colors deficient in each pixel are generated by interpolation. All the pixels are made to have the signals of the respective colors by this demosaicing processing.

The noise removing unit 58 performs noise removal processing (for example, a moving-average method, median filtering, or the like) on the image signals, which have been subjected to gamma correction and the like by the DSP 56, to remove noise from the image signals. The image signals from which noise has been removed are transmitted to the signal switching unit 60.

In a case where a mode is set to the normal observation mode by the mode changeover SW 13a, the signal switching unit 60 transmits image signals for normal light, which are obtained through the illumination of normal light and image pickup, to the normal observation image processing unit 62. Further, in a case where a mode is set to the first special observation mode, the signal switching unit 60 transmits first image signals, which are obtained through the illumination of the first illumination light and image pickup, to the first special observation image processing unit 63. The first image signals include first red color signals that are output from the R-pixels of the image pickup sensor, first green color signals that are output from the G-pixels of the image pickup sensor 48, and first blue color signals that are output from the B-pixels of the image pickup sensor 48. Furthermore, in a case where a mode is set to the second special observation mode, the signal switching unit 60 transmits second image signals, which are obtained through the illumination of the second illumination light and image pickup, to the second special observation image processing unit 64. The second image signals include second red color signals that are output from the R-pixels of the image pickup sensor, second green color signals that are output from the G-pixels of the image pickup sensor 48, and second blue color signals that are output from the B-pixels of the image pickup sensor 48. Moreover, in a case where a mode is set to the multi-observation mode, first image signals obtained through the illumination of the first illumination light and image pickup are transmitted to the first special observation image processing unit 63 and second image signals obtained through the illumination of the second illumination light and image pickup are transmitted to the second special observation image processing unit 64.

The normal observation image processing unit 62 performs image processing for a normal image on the RGB image signals that are obtained in the normal observation mode. The image processing for a normal image includes structure emphasis processing for a normal image and the like. The normal observation image processing unit 62 includes parameters for a normal image, which are to be multiplied by the RGB image signals, to perform the image processing for a normal image. The RGB image signals having been subjected to the image processing for a normal image are input to the display controller 66 from the normal observation image processing unit 62 as a normal image.

The first special observation image processing unit 63 generates the first special observation image having been subjected to image processing (image processing for a first special observation image), such as saturation emphasis processing, hue emphasis processing, and structure emphasis processing, on the basis of the first image signals. In the first special observation image, many superficial blood vessels are included and the color of the background mucous membrane is also accurately reproduced. The first special observation image processing unit 63 includes parameters for a first special observation image, which are to be multiplied by the first image signals, to perform the image processing for a first special observation image. The first special observation image processing unit 63 does not perform superficial blood vessel emphasis processing for emphasizing superficial blood vessels, but may perform the superficial blood vessel emphasis processing depending on the situation of a processing load.

Figure 9:
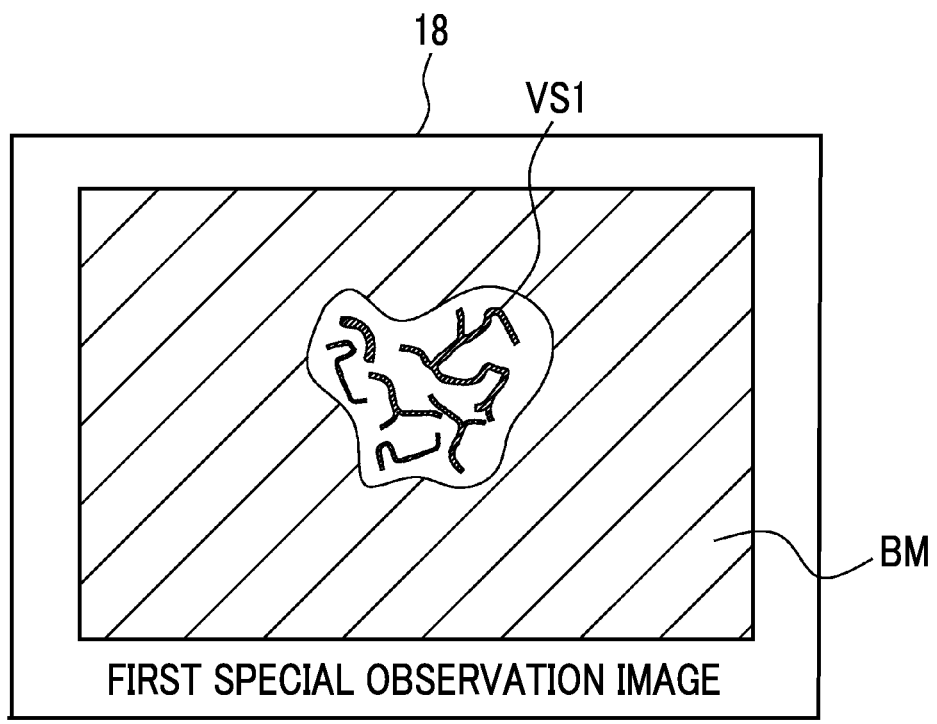
FIG. 9 is an image diagram showing a first special observation image.
Figure 10:
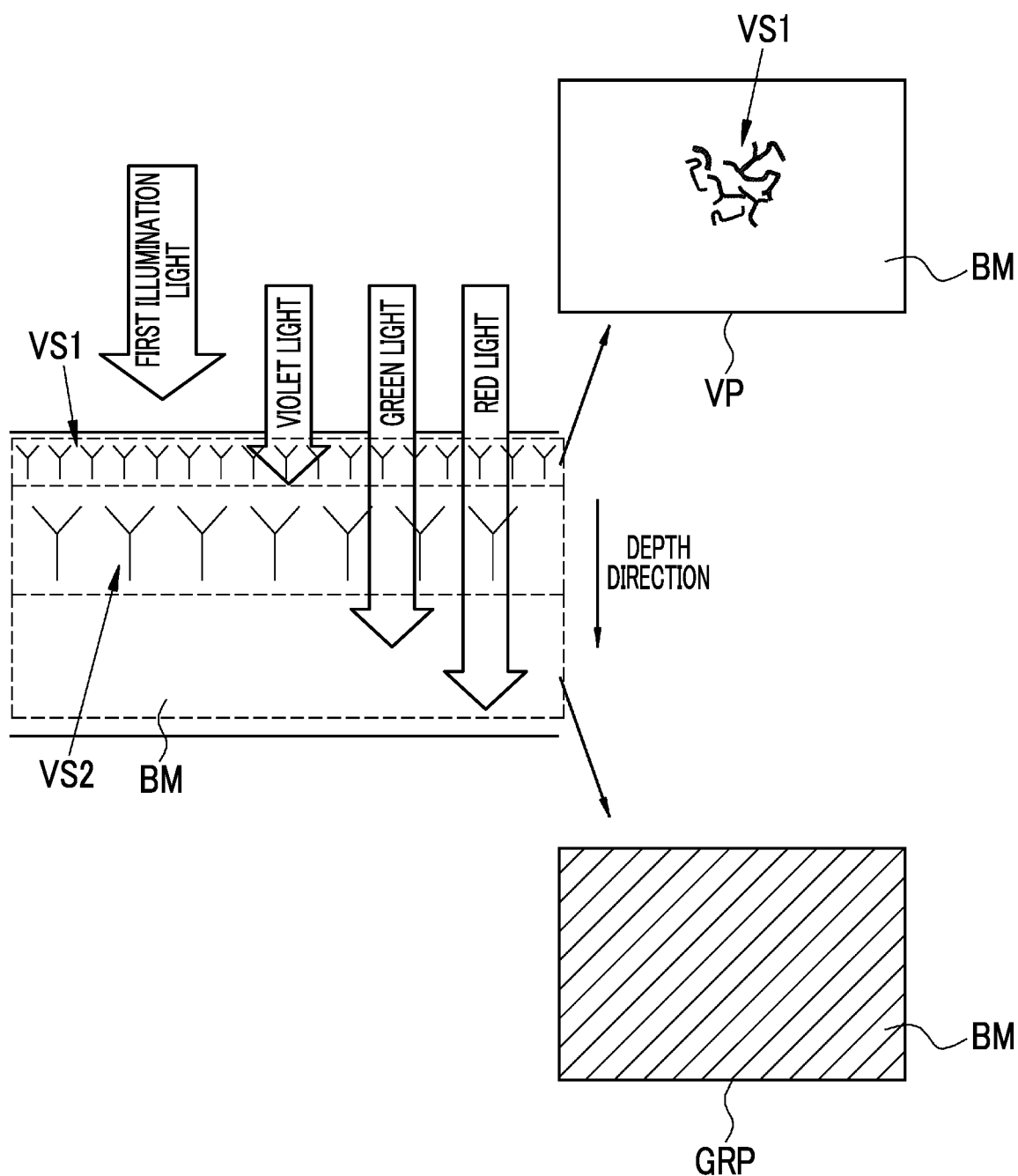
FIG. 10 is a diagram illustrating a violet light image and a green-red light image that are obtained in a case where an object is illuminated with the first illumination light.

A first special observation image in which a background mucous membrane BM of an object to be observed and superficial blood vessels VS1 are shown is displayed as the first special observation image as shown in FIG. 9. The first special observation image is obtained on the basis of the first illumination light that includes violet light, green light, and red light. In a case where an object to be observed is illuminated with the first illumination light, violet light V of the first illumination light reaches a surface layer where the superficial blood vessels VS1 are distributed as shown in FIG. 10. Accordingly, the image of the superficial blood vessels VS1 is included in a violet light image VP that is obtained on the basis of the reflected light of the violet light V. Further, green light G and red light R of the first illumination light reach the background mucous membrane BM that is distributed at a position deeper than the superficial blood vessels VS1 and intermediate blood vessels VS2 (blood vessels present at positions deeper than the superficial blood vessels VS1). Accordingly, the image of the background mucous membrane BM is included in a green-red light image GRP that is obtained on the basis of the reflected light of the green light G and the red light R. Since the first special observation image is an image in which the violet light image VP and the green-red light image GRP are combined with each other as described above, the images of the background mucous membrane BM and the superficial blood vessels VS1 are displayed.

The second special observation image processing unit 64 generates the second special observation image having been subjected to image processing (image processing for a second special observation image), such as saturation emphasis processing, hue emphasis processing, and structure emphasis processing, on the basis of the second image signals. In the second special observation image, many intermediate blood vessels are included and the color of the background mucous membrane is also accurately reproduced. The second special observation image processing unit 64 includes parameters for a second special observation image, which are to be multiplied by the second image signals, to perform the image processing for a second special observation image. The second special observation image processing unit 64 does not perform intermediate blood vessel emphasis processing for emphasizing intermediate blood vessels, but may perform the intermediate blood vessel emphasis processing depending on the situation of a processing load.

Figure 11:
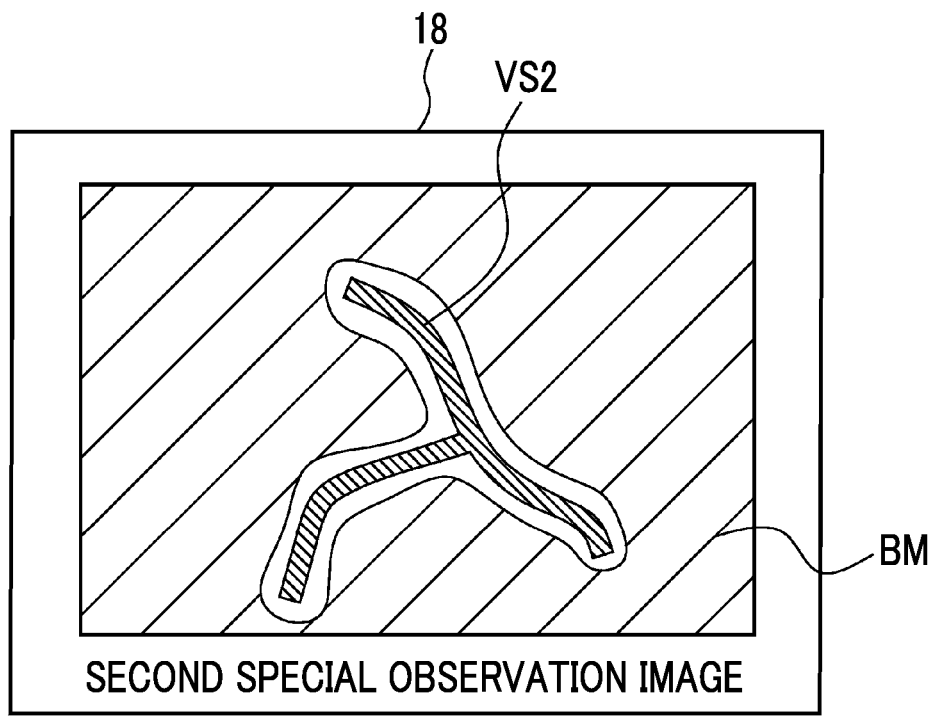
FIG. 11 is an image diagram showing a second special observation image.
Figure 12:
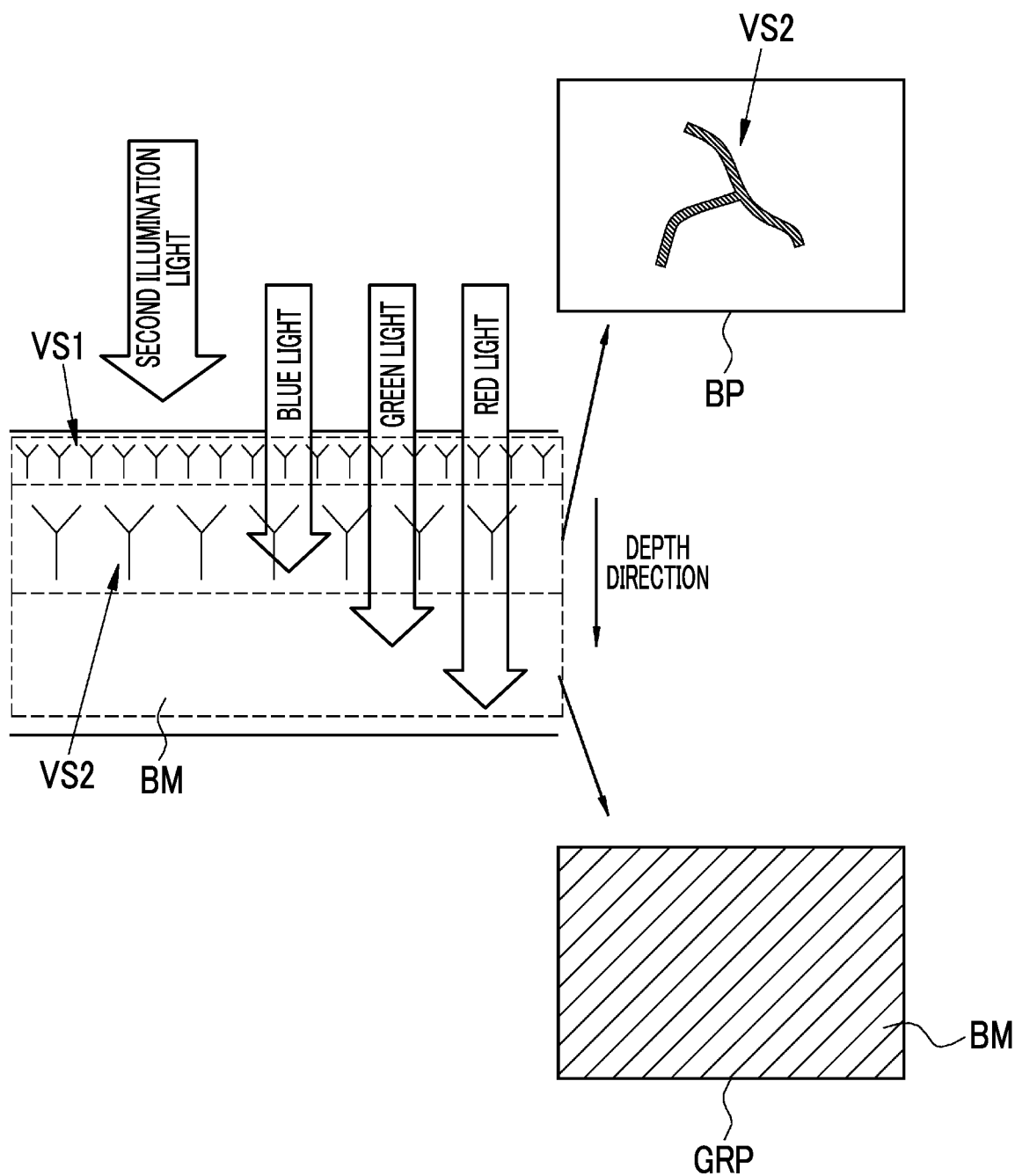
FIG. 12 is a diagram illustrating a blue light image and a green-red light image that are obtained in a case where an object is illuminated with the second illumination light.
Figure 13:
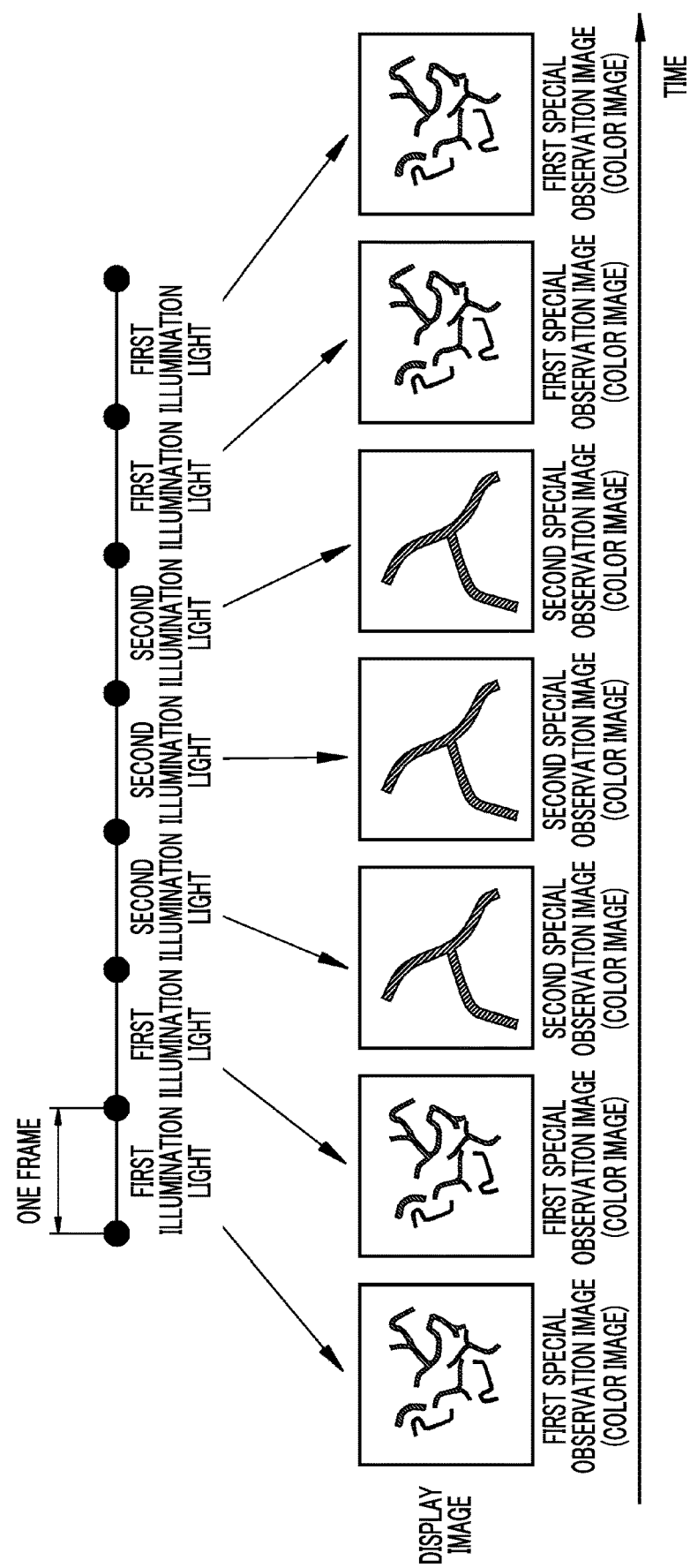
FIG. 13 is a diagram illustrating the switching display of a first special observation image and a second special observation image that are color images.

A second special observation image in which a background mucous membrane BM of an object to be observed and intermediate blood vessels VS2 are shown is displayed as the second special observation image as shown in FIG. 11. The second special observation image is obtained on the basis of the second illumination light that includes blue light, green light, and red light. In a case where the object to be observed is illuminated with the second illumination light, blue light B of the second illumination light reaches an intermediate layer where the intermediate blood vessels VS2 are distributed as shown in FIG. 12. Accordingly, the image of the intermediate blood vessels VS2 is included in a blue light image BP that is obtained on the basis of the reflected light of the blue light B. Further, green light G and red light R of the second illumination light reach the background mucous membrane BM that is distributed at a position deeper than the superficial blood vessels VS1 and the intermediate blood vessels VS2 (blood vessels present at positions deeper than the superficial blood vessels VS1). Accordingly, the image of the background mucous membrane BM is included in a green-red light image GRP that is obtained on the basis of the reflected light of the green light G and the red light R. Since the second special observation image is an image in which the blue light image BP and the green-red light image GRP are combined with each other as described above, the images of the background mucous membrane BM and the intermediate blood vessels VS2 are displayed.

The display controller 66 performs control to display the normal image, the first special observation image, or the second special observation image, which are input from the normal observation image processing unit 62, the first special observation image processing unit 63, or the second special observation image processing unit 64, as images that can be displayed on the monitor 18. An image corresponding to each observation mode is displayed by the control of the display controller 66. In the normal observation mode, the normal image is displayed on the monitor 18. Further, the first special observation image (see FIG. 9) is displayed on the monitor 18 in the first special observation mode. Furthermore, the second special observation image (see FIG. 11) is displayed on the monitor 18 in the second special observation mode.

Moreover, in the multi-observation mode, the first special observation image and the second special observation image, which are color images, are switched and displayed on the monitor 18 according to the light emission period of the first illumination light and the light emission period of the second illumination light. That is, in a case where the light emission period of the first illumination light is two frames and the light emission period of the second illumination light is three frames, the first special observation image continues to be displayed for two frames and the second special observation image continues to be displayed for three frames.

As described above, two kinds of the first and second special observation images can be automatically switched and displayed in the multi-observation mode without the operation of the mode changeover SW 13a that is performed by a user. Since the first and second special observation images are automatically switched and displayed as described above, the same object to be observed is displayed in the first and second special observation images as long as the object to be observed is not moved or the distal end part 12d of the endoscope 12 is not moved. However, since the spectral information of the first special observation image and the spectral information of the second special observation image are different from each other even in the case of the same object to be observed, the object to be observed looks different depending on a difference in spectral information. That is, the visibility of the superficial blood vessels is high in the first special observation image, but the visibility of the intermediate blood vessels is high in the second special observation image. Accordingly, since the first and second special observation images are switched and displayed, the visibility of a plurality of blood vessels having different depths can be improved.

Figure 14:
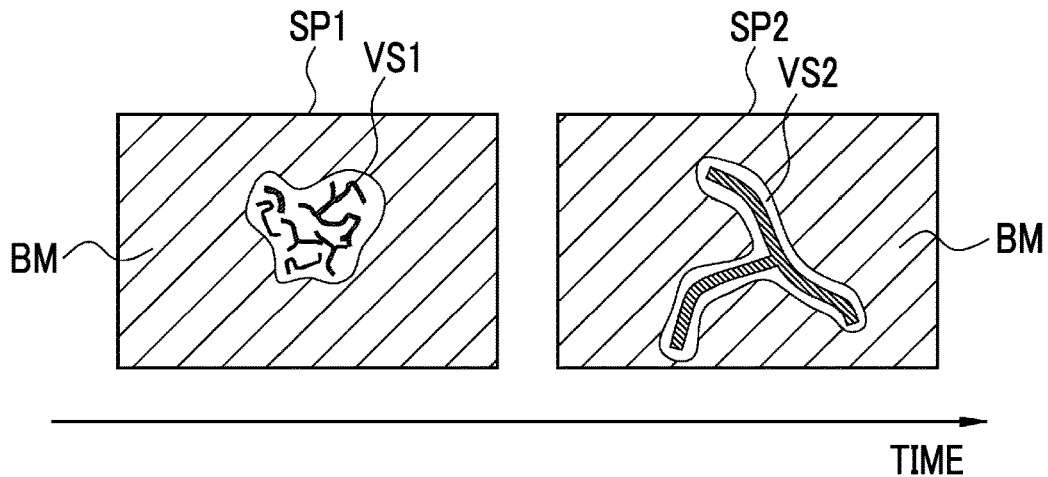
FIG. 14 is a diagram illustrating the switching display of a first special observation image and a second special observation image of which the tints of background mucous membranes match.

Further, since the light amount condition of the first illumination light and the light amount condition of the second illumination light used in the multi-observation mode are set to the specific light amount conditions and light is emitted, the tint of a background mucous membrane BM of a first special observation image SP1 and the tint of a background mucous membrane BM of a second special observation image SP2 match as shown in FIG. 14. The reason for this is that the signal value of a first blue color signal for specific biological tissue among first blue color signals included in the first special observation image is equal to the signal value of a second blue color signal for specific biological tissue among second blue color signals included in the second special observation image. Since the first and second special observation images SP1 and SP2 of which the background mucous membranes BM match are switched and displayed as described above, only differences between superficial components and intermediate components are changed, that is, the superficial blood vessels and the intermediate blood vessels are switched and displayed. Accordingly, the superficial components and the intermediate components can be visually recognized.

Figure 15:
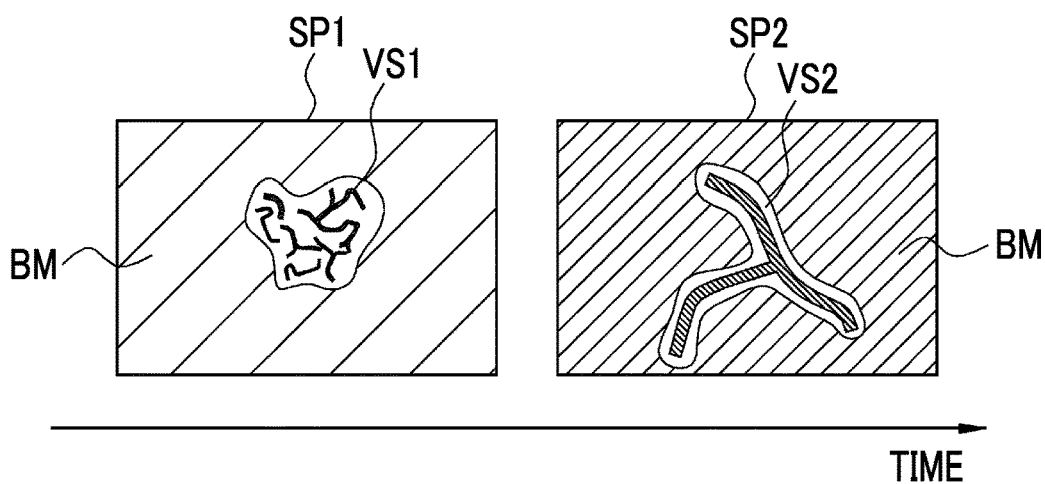
FIG. 15 is a diagram illustrating the switching display of a first special observation image and a second special observation image of which the tints of background mucous membranes are different from each other.
Figure 16:
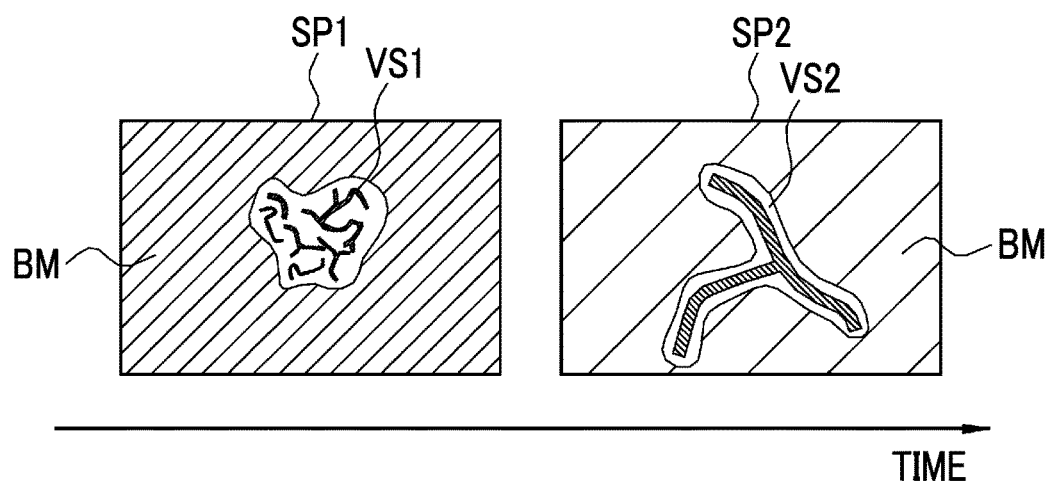
FIG. 16 is a diagram illustrating the switching display of a first special observation image and a second special observation image of which the tints of background mucous membranes are different from each other.

On the other hand, in a case where the signal value of the first blue color signal is larger than the signal value of the second blue color signal, the background mucous membrane BM of the first special observation image SP1 has a blue color but the background mucous membrane BM of the second special observation image SP2 has a yellow color as shown in FIG. 15. For this reason, the tint of the background mucous membrane BM of the first special observation image SP1 and the tint of the background mucous membrane BM of the second special observation image SP2 are different from each other. Accordingly, it is not possible to visually recognize which portions are the superficial blood vessels VS1 or the intermediate blood vessels VS2. In contrast, in a case where the signal value of the first blue color signal is smaller than the signal value of the second blue color signal, the background mucous membrane BM of the first special observation image SP1 has a yellow color but the background mucous membrane BM of the second special observation image SP2 has a blue color as shown in FIG. 16. Even in this case, the tint of the background mucous membrane BM of the first special observation image SP1 and the tint of the background mucous membrane BM of the second special observation image SP2 are different from each other. Accordingly, it is not possible to visually recognize which portions are the superficial blood vessels VS1 or the intermediate blood vessels VS2.

The static image-storage controller 68 performs control to store an image, which is obtained according to the instruction of the static image-acquisition instruction unit 13b at the timing of a static image-acquisition instruction, in the static image storage unit 67 as a static image. In the normal observation mode, the static image-storage controller 68 stores a normal image, which is obtained at the timing of the static image-acquisition instruction, in the static image storage unit 67 as a static image. In the first special observation mode, the static image-storage controller 68 stores a first special observation image, which is obtained at the timing of the static image-acquisition instruction, in the static image storage unit 67 as a static image. In the second special observation mode, the static image-storage controller 68 stores a second special observation image, which is obtained at the timing of the static image-acquisition instruction, in the static image storage unit 67 as a static image. Further, in the multi-observation mode, the static image-storage controller 68 stores a set of observation images for display, which is formed of the first special observation image and the second special observation image obtained at the timing of the static image-acquisition instruction, in the static image storage unit 67.

Next, the details of the specific light amount conditions will be described. The specific light amount conditions are the light amount condition of the first illumination light and the light amount condition of the second illumination light determined so that the signal value of the first blue color signal for specific biological tissue and the signal value of the second blue color signal for specific biological tissue are equal to each other. In the first embodiment, on the premise that the spectral reflectivity $S(\lambda)$ of specific biological tissue is already known, a first calculation value B1 is used as a value corresponding to the signal value of a first blue color signal used to calculate a specific light amount condition and a second calculation value B2 is used as a value corresponding to the signal value of a second blue color signal used to calculate a specific light amount condition.

Figure 17:
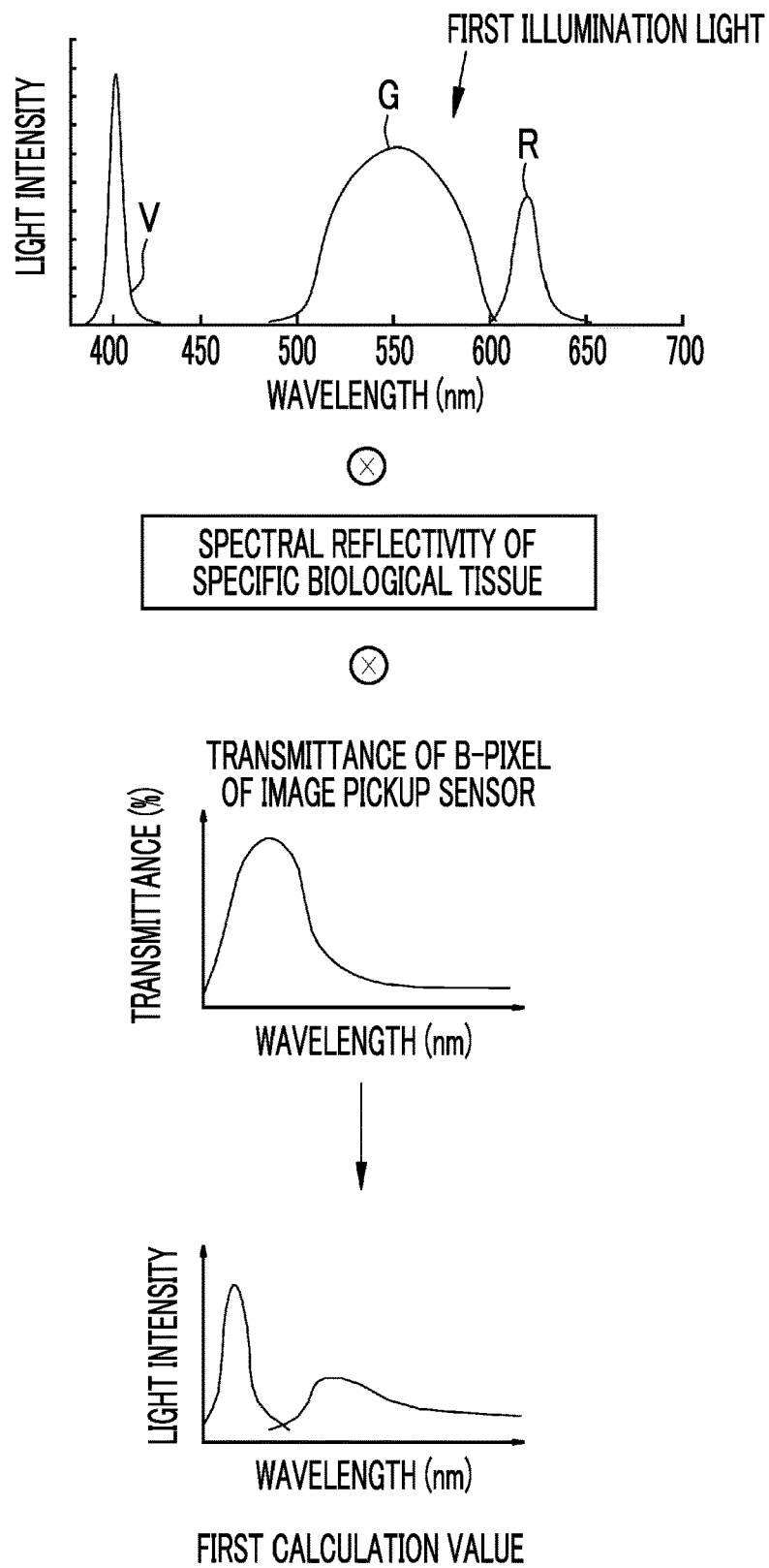
FIG. 17 is a diagram illustrating a method of calculating a first calculation value.

As shown in FIG. 17, the first calculation value B1 is obtained from Equation 1) on the basis of the light intensity $E1(\lambda)$ of the first illumination light, the spectral reflectivity $S(\lambda)$ of specific biological tissue, and the spectral sensitivity $b(\lambda)$ of the B-pixel of the image pickup sensor 48 (sensitivity is expressed as "transmittance (%)" in FIG. 17).

$$B1=\int E1(\lambda)\times S(\lambda)\times b(\lambda)d\lambda \qquad \text{Equation 1)}$$

Figure 18:
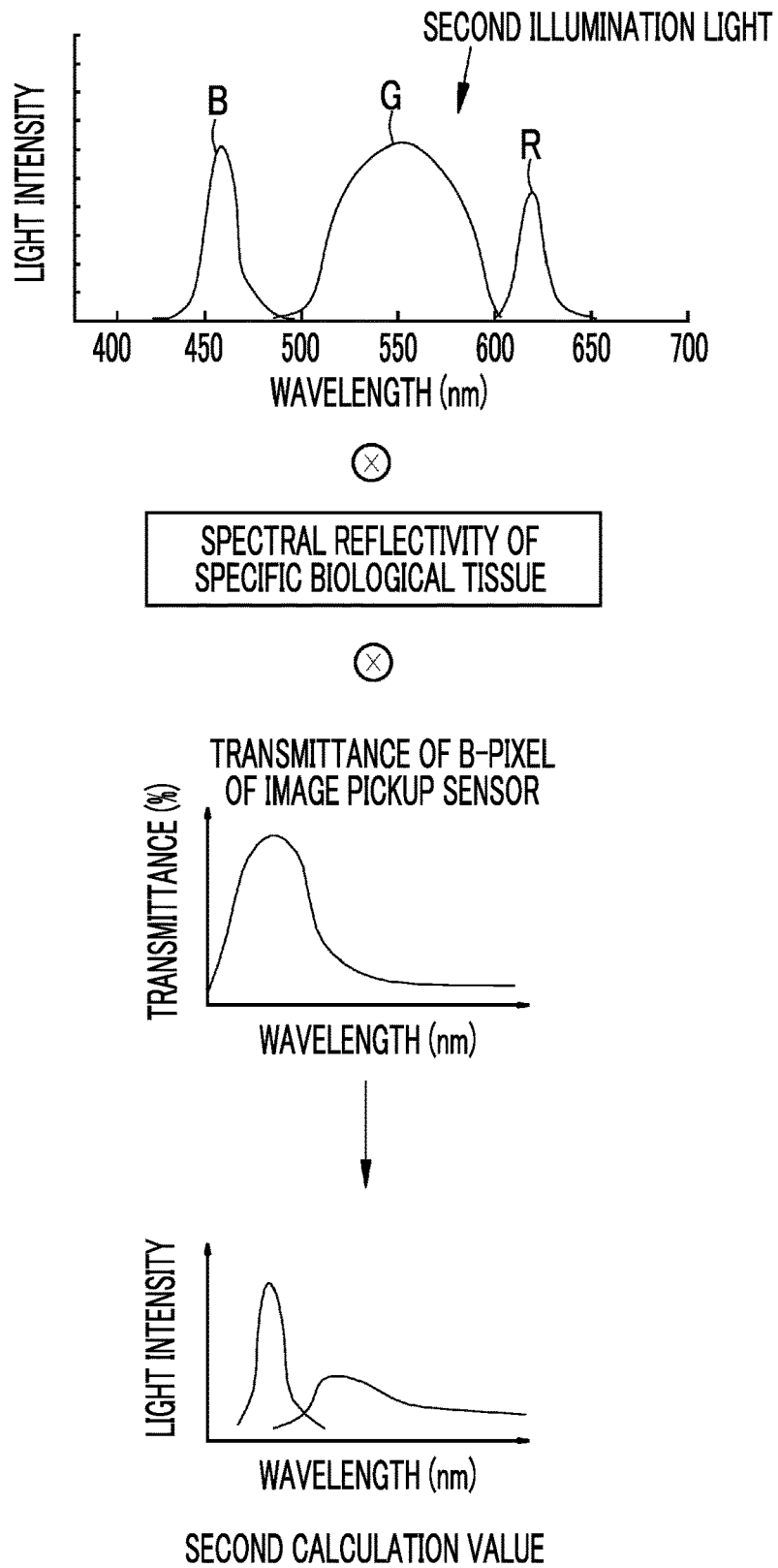
FIG. 18 is a diagram illustrating a method of calculating a second calculation value.

As shown in FIG. 18, the second calculation value is obtained from Equation 2) on the basis of the light intensity $E2(\lambda)$ of the second illumination light, the spectral reflectivity $S(\lambda)$ of specific biological tissue, and the spectral sensitivity $b(\lambda)$ of the B-pixel of the image pickup sensor 48 (sensitivity is expressed as "transmittance (%)" in FIG. 18).

$$B2=\int E2(\lambda)\times S(\lambda)\times b(\lambda)d\lambda \qquad \text{Equation 2)}$$

The light intensity $E1(\lambda)$ of the first illumination light and the light intensity $E2(\lambda)$ of the second illumination light are determined so that the first calculation value B1 obtained from Equation 1) and the second calculation value B2 obtained from Equation 2) are equal to each other. Here, the first calculation value B1 and the second calculation value B2 are made to be equal to each other through the adjustment of the light intensity (Vs1) of violet light V and the light intensity (Bs2) of blue light B in a state where the light intensities (Gs1 and Rs1) of green light G and red light R included in the first illumination light are equal to the light intensities (Gs2 and Rs2) of green light G and red light R included in the second illumination light. The light intensity $E1(\lambda)$ of the first illumination light and the light intensity $E2(\lambda)$ of the second illumination light, which are obtained in a case where the first calculation value B1 and the second calculation value B2 are made to be equal to each other, are set as the specific light amount conditions. A case where the first calculation value B1 and the second calculation value B2 are equal to each other includes a case where a difference between the first calculation value B1 and the second calculation value B2 is in a certain allowable range even though the first calculation value B1 and the second calculation value B2 are different from each other, in addition to a case where the first calculation value B1 and the second calculation value are completely equal to each other.

Figure 19:
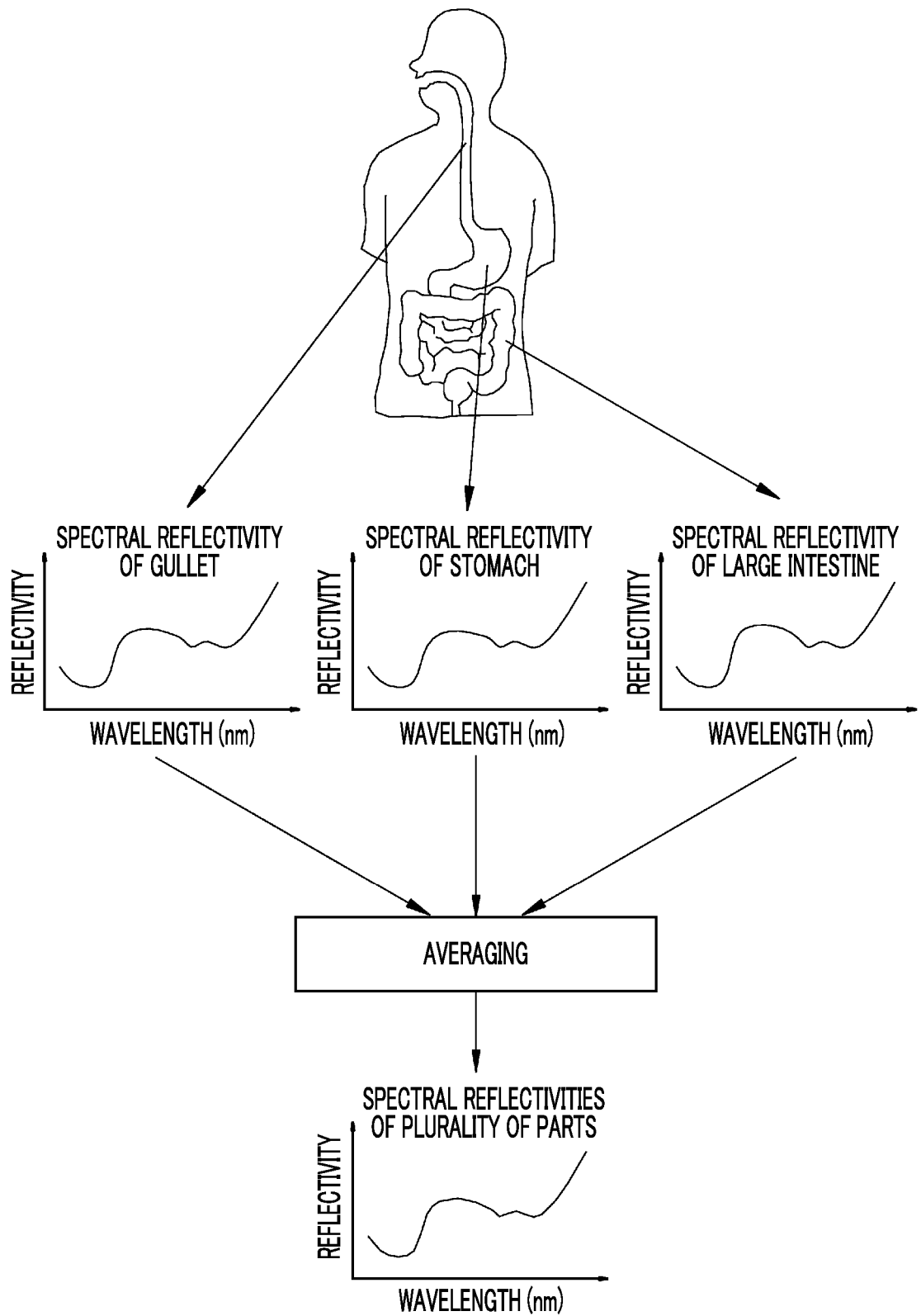
FIG. 19 is a diagram illustrating the average spectral reflectivity of a plurality of parts.

For example, the spectral reflectivities of biological tissue of a plurality of parts may be used as the spectral reflectivity of specific biological tissue. Specifically, as shown in FIG. 19, the average spectral reflectivity of a plurality of parts, which is obtained by the averaging of the spectral reflectivity of the gullet, the spectral reflectivity of the stomach, and the spectral reflectivity of the large intestine, is defined as the spectral reflectivity of specific biological tissue. It is preferable that the reflectivity (already known) of a standard human body is used for each of the spectral reflectivity of the gullet, the spectral reflectivity of the stomach, and the spectral reflectivity of the large intestine.

Figure 20:
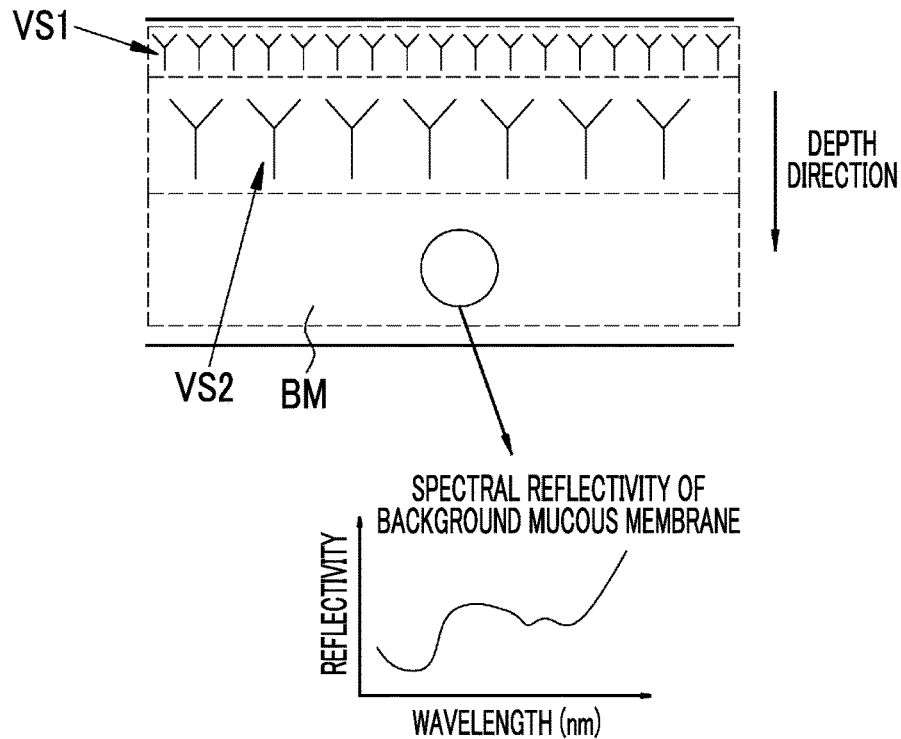
FIG. 20 is a diagram illustrating the spectral reflectivity of a background mucous membrane.

Further, for example, the spectral reflectivity (already known) of the background mucous membrane BM, which is a part of biological tissue, may be used as the spectral reflectivity of specific biological tissue as shown in FIG. 20. The spectral reflectivity of the background mucous membrane BM may be the spectral reflectivity of a background mucous membrane that is included in any one of parts, such as the gullet, the stomach, and the large intestine; or may be an average value of the spectral reflectivities of the background mucous membranes included in the respective parts.

Figure 21:
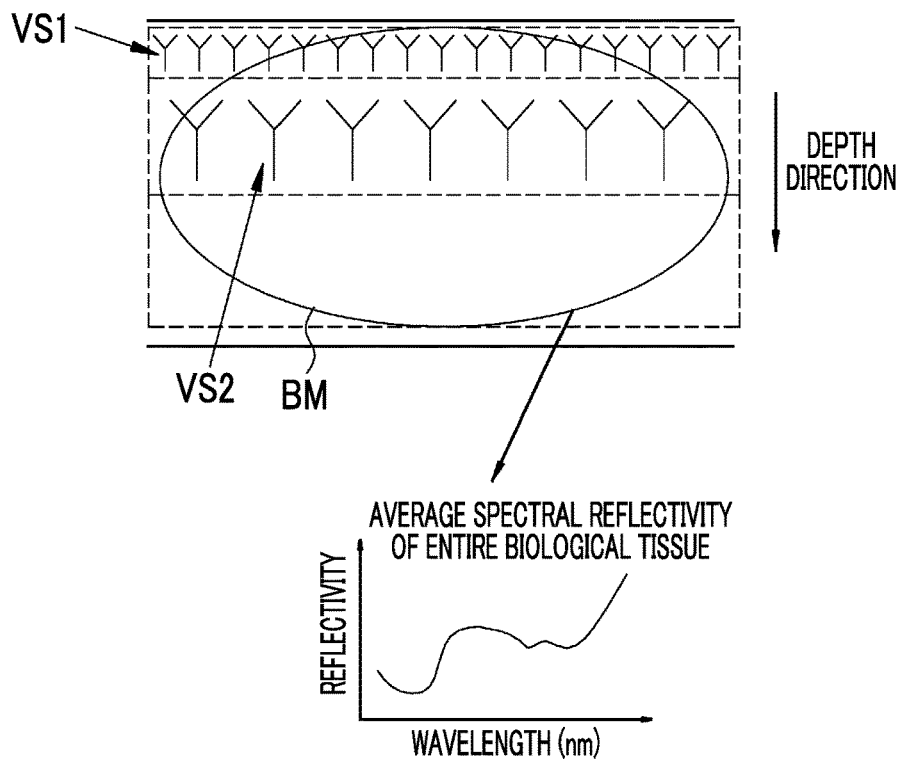
FIG. 21 is a diagram illustrating the average spectral reflectivity of the entire biological tissue.

Furthermore, for example, the average spectral reflectivity of the entire biological tissue including the superficial blood vessels VS1, the intermediate blood vessels VS2, and the background mucous membrane BM may be used as the spectral reflectivity of specific biological tissue as shown in FIG. 21. Specifically, the average value of the spectral reflectivity of the superficial blood vessels VS1, the spectral reflectivity of the intermediate blood vessels VS2, and the spectral reflectivity of the background mucous membrane BM may be used as the average spectral reflectivity of the entire biological tissue.

Figure 22:
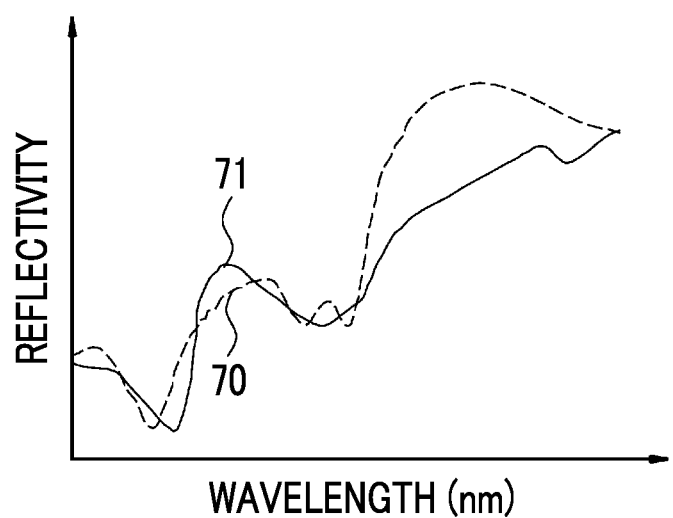
FIG. 22 is a graph showing the spectral reflectivities of a high-oxygen portion and a low-oxygen portion.
Figure 23:
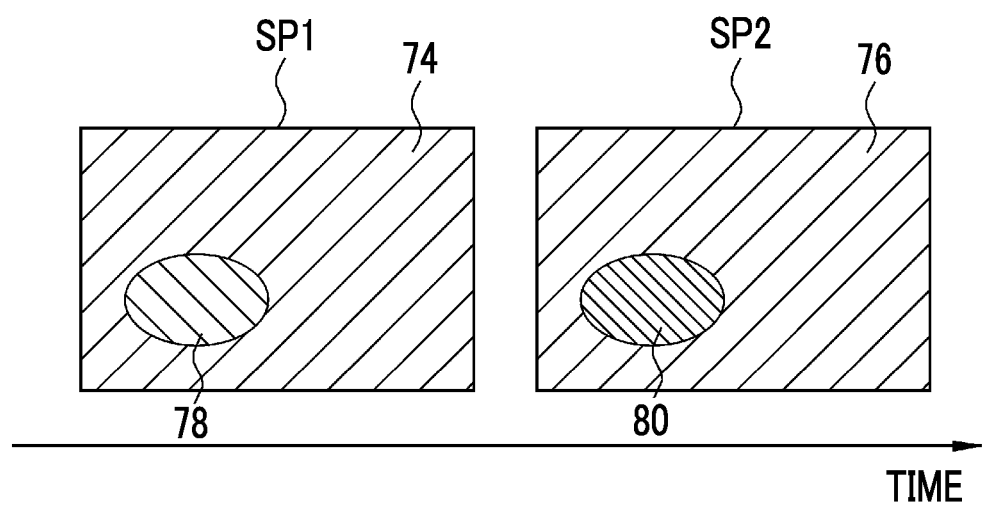
FIG. 23 is a diagram illustrating the switching display of a first special observation image and a second special observation image of which the tints of high-oxygen portions match.

Further, any one of the spectral reflectivity of a high-oxygen portion of biological tissue that includes a specific percentage or higher of oxyhemoglobin in blood vessels, or the spectral reflectivity of a low-oxygen portion of biological tissue that includes a specific percentage or higher of reduced hemoglobin in blood vessels may be used as the spectral reflectivity of specific biological tissue. As shown in FIG. 22, the spectral reflectivity of the high-oxygen portion is shown by a graph 70 and the spectral reflectivity of the low-oxygen portion is shown by a graph 71. For example, in a case where the spectral reflectivity of the high-oxygen portion is used as the spectral reflectivity of specific biological tissue to determine a specific light amount condition, the tint of a high-oxygen portion 74 of the first special observation image SP1 and the tint of a high-oxygen portion 76 of the second special observation image SP2 match as shown in FIG. 23. On the other hand, the tint of a low-oxygen portion 78 of the first special observation image SP1 and the tint of a low-oxygen portion 80 of the second special observation image are different from each other.

Accordingly, in a case where the first special observation image SP1 and the second special observation image SP2 are switched and displayed, the low-oxygen portion 78 of the first special observation image SP1 and the low-oxygen portion 80 of the second special observation image are displayed so as to flicker. Since the low-oxygen portions 78 and 80 are displayed so as to flicker as described above, the low-oxygen portions 78 and 80 can be visually recognized even though the low-oxygen portions 78 and 80 have low contrast in the images. In a case where the spectral reflectivity of the low-oxygen portion is used as the spectral reflectivity of specific biological tissue to determine a specific light amount condition, the tints of the low-oxygen portions of the first and second special observation images match and the high-oxygen portions are displayed so as to flicker by the switching of the first and second special observation images.

Figure 24:
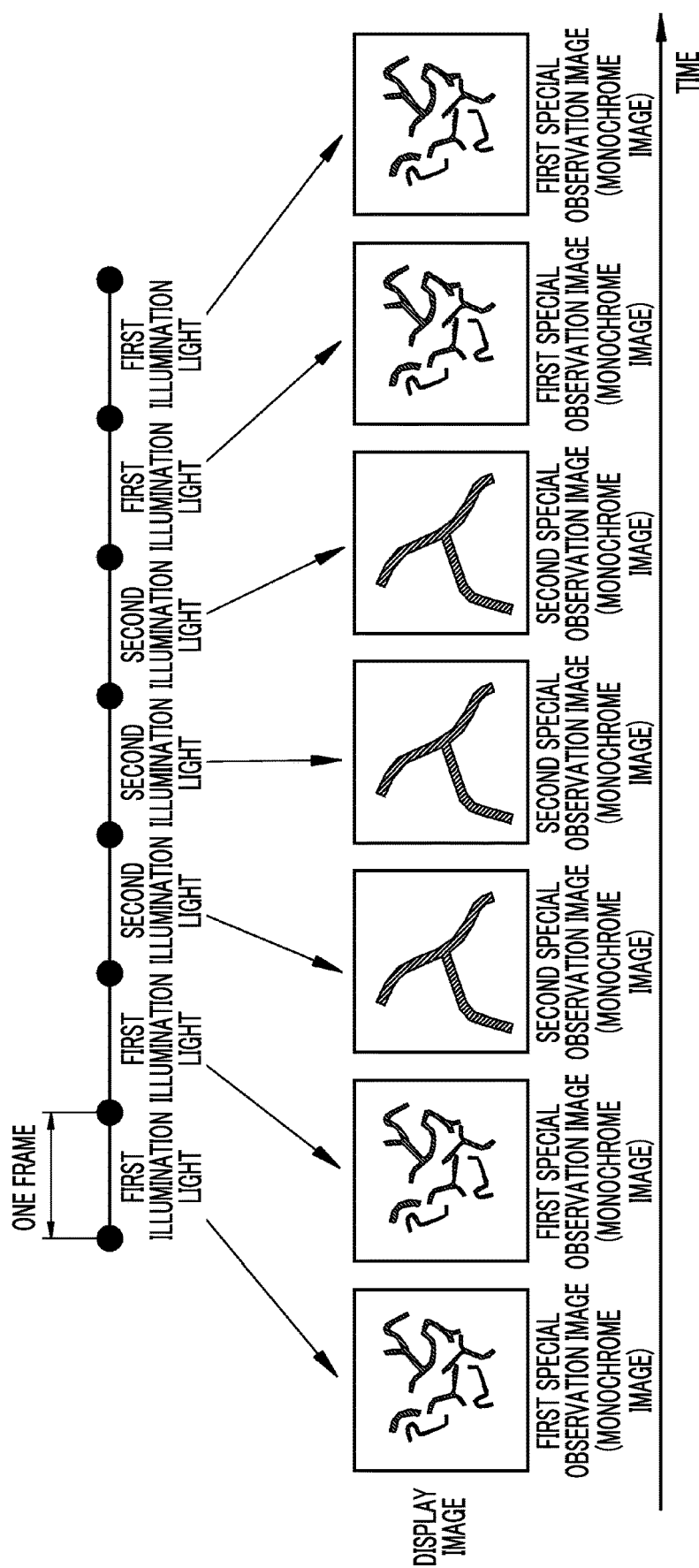
FIG. 24 is a diagram illustrating the switching display of a first special observation image and a second special observation image that are monochrome images.

The first and second special observation images are displayed in the multi-observation mode as color images, but the first and second special observation images may be displayed as monochrome images instead of color images as shown in FIG. 24. In a case where the first and second special observation images as monochrome images are switched and displayed in this way, a change in color hardly occurs at portions other than blood vessels, such as superficial blood vessels and intermediate blood vessels. Accordingly, a user can pay attention to and observe blood vessels having different depths, such as superficial blood vessels and intermediate blood vessels, without a sense of incongruity in the case of the switching of the first and second special observation images.

Figure 25:
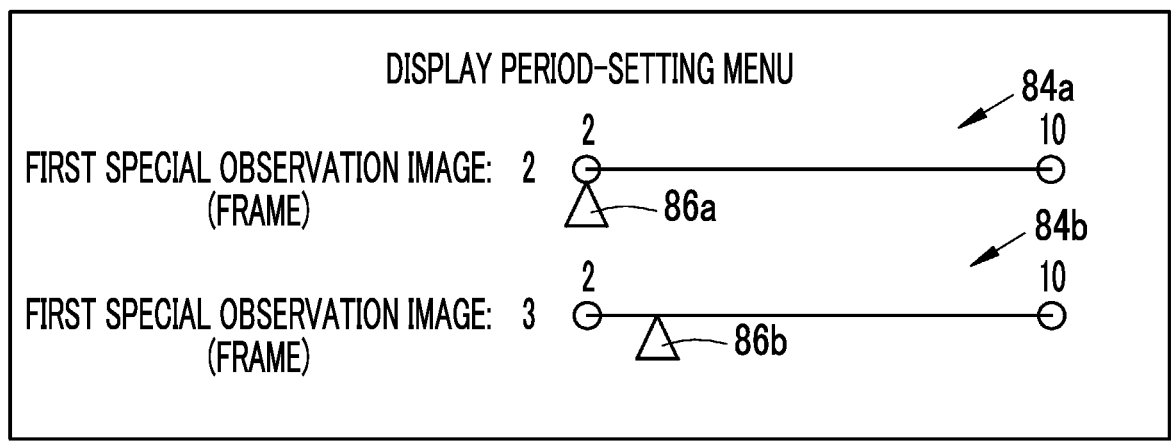
FIG. 25 is a diagram illustrating a display period-setting menu.

The display period of the first special observation image and the display period of the second special observation image can be appropriately changed by a display period-setting unit 66*a* that is provided in the display controller 66 (see FIG. 2). In a case where an operation for changing a display period is received by the operation of the user interface 19, the display period-setting unit 66*a* displays a display period-setting menu shown in FIG. 25 on the monitor 18. The display period of the first special observation image can be changed between, for example, two frames and ten frames. Each display period is assigned to a slide bar 84*a*.

In a case where the display period of the first special observation image is to be changed, a user operates the user interface 19 to position a slider 86*a* at a position on the slide bar 84*a* that represents a display period to which the user wants to change a display period. Accordingly, the display period of the first special observation image is changed. Even in the case of the display period of the second special observation image, a user operates the user interface 19 to position a slider 86*b* at a position on a slide bar 84*b* (to which a display period in the range of, for example, two frames to ten frames is assigned) that represents a display period to which the user wants to change a display period. Accordingly, the display period of the second special observation image is changed.

In a case where the light emission period of the first illumination light is shorter than the display period of the first special observation image, it is preferable that a first special observation image corresponding to the display period is generated by complementary processing or the like so as to be displayed for the display period of the first special observation image. In contrast, in a case where the light emission period of the second illumination light is longer than the display period of the first special observation image, the first special observation image may not be used for display according to the display period of the first special observation image. Further, it is preferable that the display periods of the first and second special observation images are set to at least two or more frames. Since the images are quickly switched in a case where the display periods of the first and second special observation images are set to one frame, there is a concern that a user cannot recognize a difference between the first and second special observation images.

Figure 26:
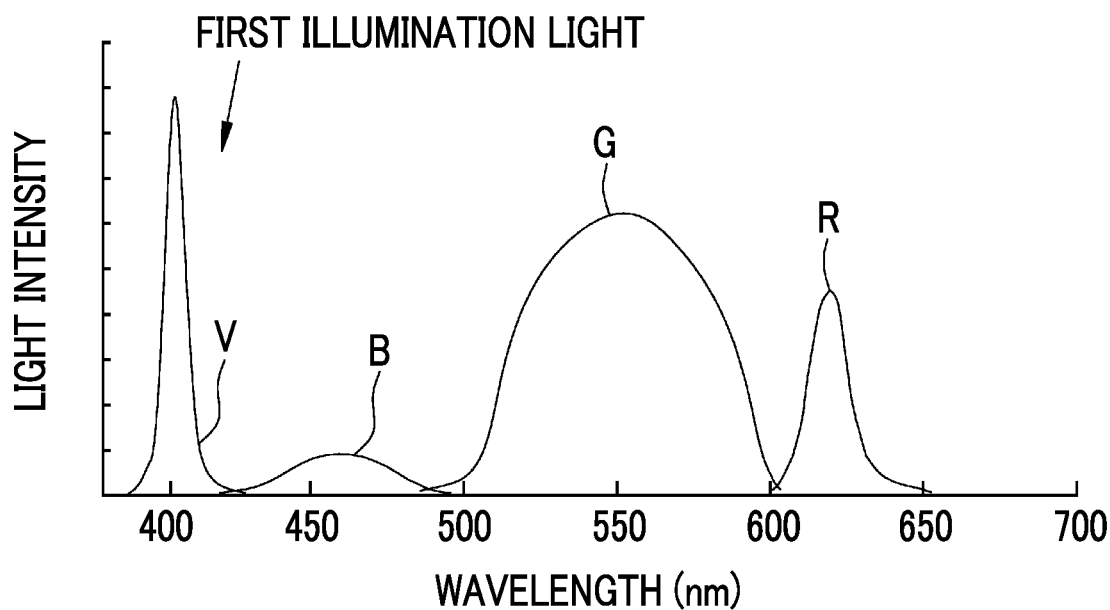
FIG. 26 is a graph showing the emission spectrum of first illumination light that includes violet light V, blue light B, green light G, and red light R.
Figure 27:
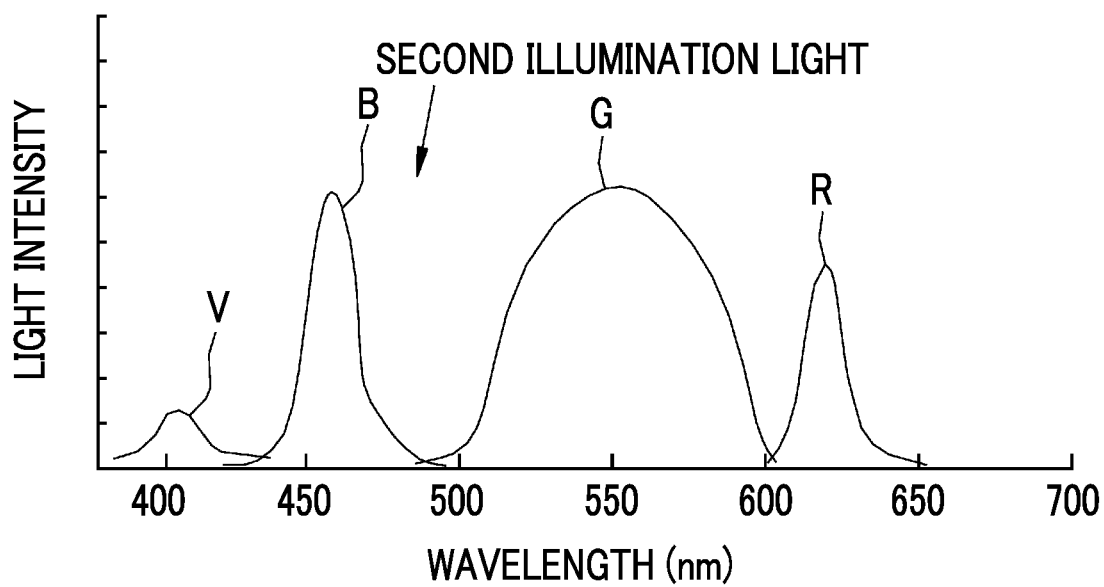
FIG. 27 is a graph showing the emission spectrum of second illumination light that includes violet light V, blue light B, green light G, and red light R.

The first illumination light includes violet light V, green light G, and red light R in the embodiment. However, as shown in FIG. 26, blue light B may be added to the first illumination light so that the first illumination light includes violet light V, blue light B, green light G, and red light R. In this case, the light intensity of violet light V is set to be higher than the light intensity of blue light B. For example, it is preferable that a ratio between the light intensity Vs1 of violet light V and the light intensity Bs1 of blue light B is set to "9:1". Further, the second illumination light includes blue light B, green light G, and red light R. However, as shown in FIG. 27, violet light V may be added to the second illumination light so that the second illumination light includes violet light V, blue light B, green light G, and red light R. In this case, the light intensity of blue light B is set to be higher than the light intensity of violet light V. For example, it is preferable that a ratio between the light intensity Vs2 of violet light V and the light intensity Bs2 of blue light B is set to "1:9". In a case where each of the first illumination light and the second illumination light includes violet light V, blue light B, green light G, and red light R as described above, it is preferable that the intensity ratio of violet light included in the first illumination light and the intensity ratio of violet light included in the second illumination light are set to be different from each other and the intensity ratio of blue light included in the first illumination light and the intensity ratio of blue light included in the second illumination light are set to be different from each other in a state where the light intensity ratios of green light and red light included in the first illumination light are equal to the light intensity ratios of green light and red light included in the second illumination light.

Figure 28:
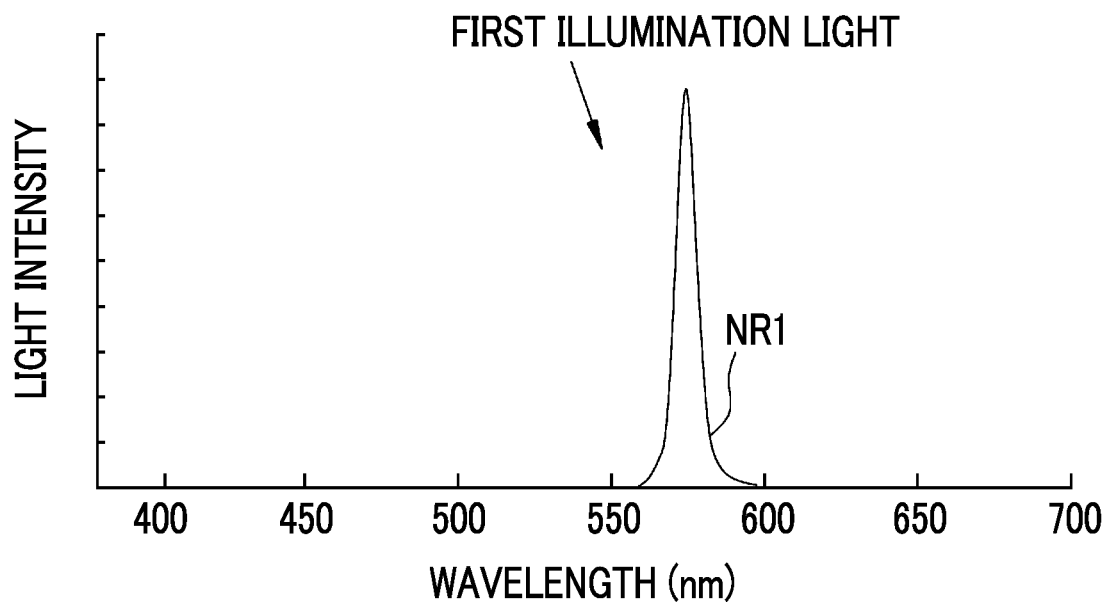
FIG. 28 is a graph showing the emission spectrum of first illumination light including first red narrow-band light.
Figure 29:
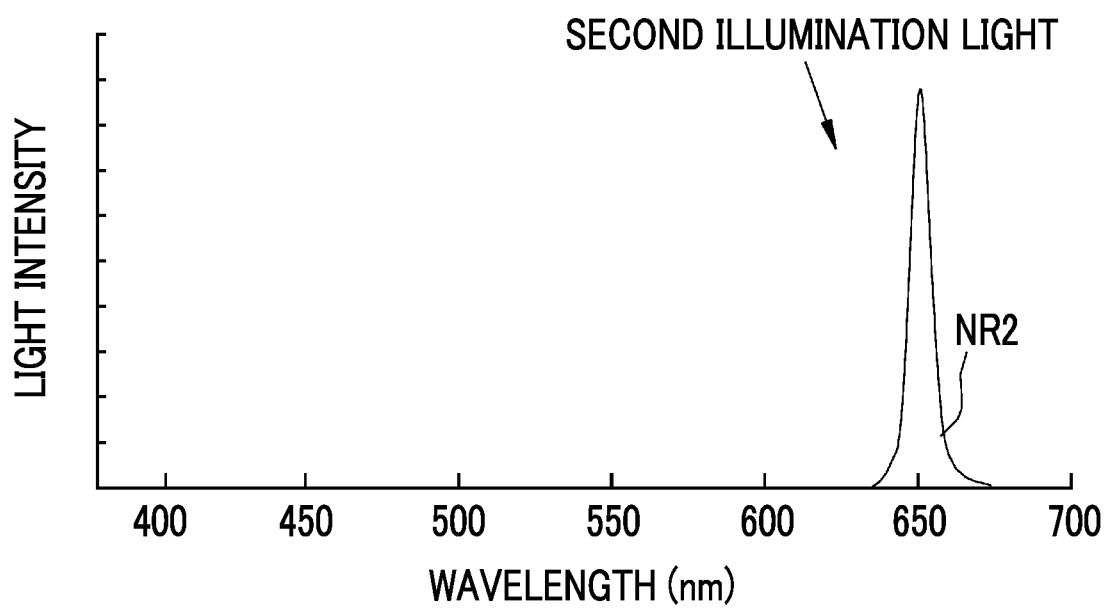
FIG. 29 is a graph showing the emission spectrum of first illumination light including second red narrow-band light.

Further, first red narrow-band light NR1 of which the central wavelength or the peak wavelength is in the range of 560 to 580 nm as shown in FIG. 28 may be included in the first illumination light instead of violet light V, green light G, and red light R. Furthermore, second red narrow-band light NR2 of which the central wavelength or the peak wavelength is in the range of 630 to 670 nm as shown in FIG. 29 may be included in the second illumination light instead of blue light B, green light G, and red light R. In this case, it is preferable that specific light amount conditions (the light amount condition of the first red narrow-band light NR1 and the light amount condition of the second red narrow-band light NR2) are determined so that the signal value of a first red color signal (first specific color signal) for specific biological tissue corresponding to at least specific biological tissue among first image signals obtained in a case where the image of an object to be observed is picked up using the first red narrow-band light NR1 is equal to the signal value of a second red color signal (second specific color signal) for specific biological tissue corresponding to at least the specific biological tissue among second image signals obtained in a case where the image of the object to be observed is picked up using the second red narrow-band light NR2. Each of the first red narrow-band light NR1 and the second red narrow-band light NR2 has sensitivity to the R-pixel of the image pickup sensor 48.

Figure 30:
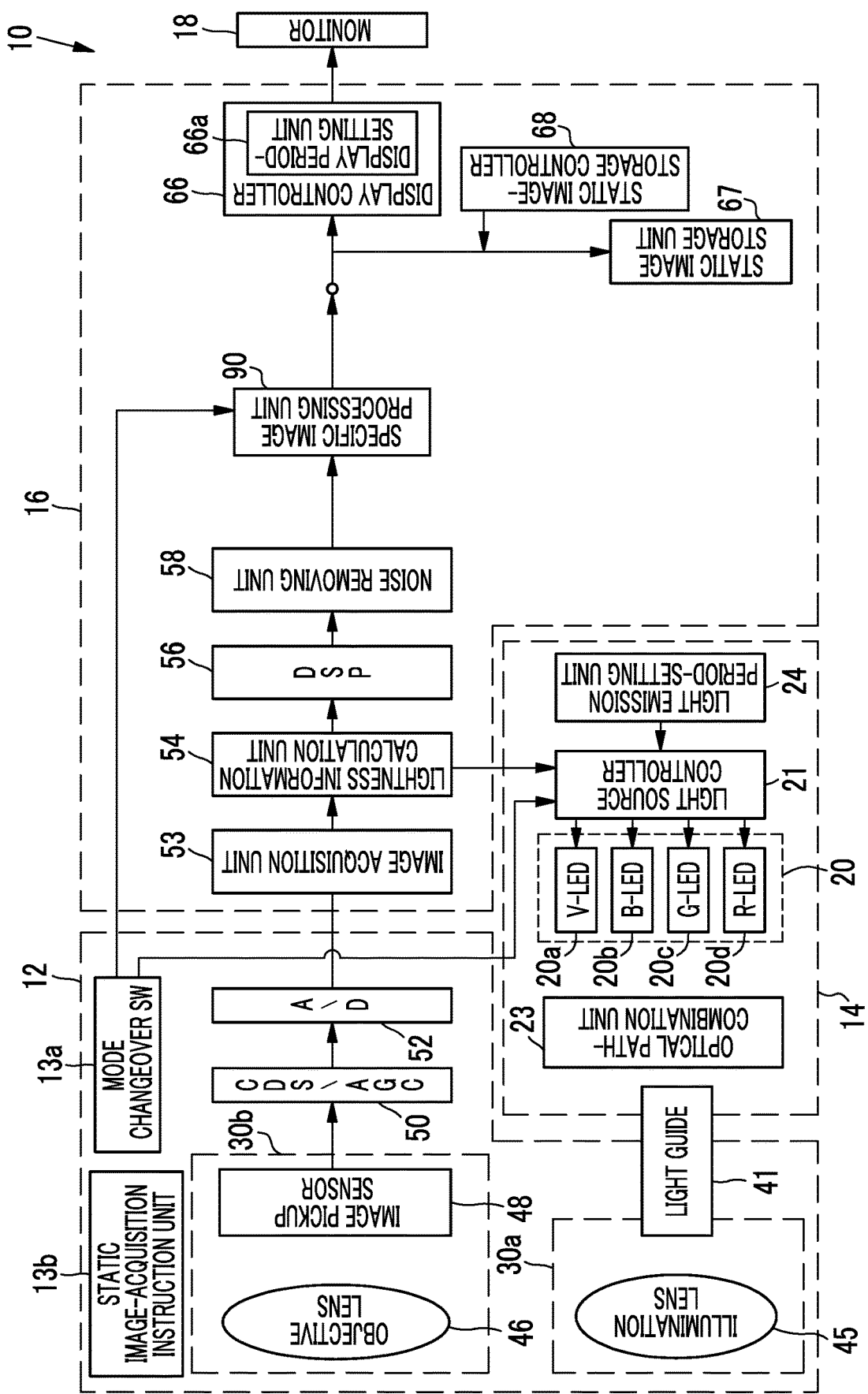
FIG. 30 is a block diagram showing the functions of an endoscope system according to another aspect of the first embodiment.

In the embodiment, the normal observation image processing unit 62, the first special observation image processing unit 63, and the second special observation image processing unit 64 are provided and a processing unit to be used to perform processing is determined according to an observation mode by the signal switching unit 60 (see FIG. 2). However, processing may be performed by other methods. For example, a specific image processing unit 90, which is a combination of these processing units 62, 63, and 64, may be provided as shown in FIG. 30 instead of the normal observation image processing unit 62, the first special observation image processing unit 63, and the second special observation image processing unit 64; and image processing corresponding to each observation mode may be performed using a parameter corresponding to the observation mode.

For example, in the normal observation mode, the specific image processing unit 90 sets a parameter to a parameter for a normal image and performs image processing to generate a normal image. In the first special observation mode, the specific image processing unit 90 sets a parameter to a parameter for a first special observation image and generates a first special observation image. In the second special observation mode, the specific image processing unit 90 sets a parameter to a parameter for a second special observation image and generates a second special observation image. In the multi-observation mode, the specific image processing unit 90 generates each of the first and second special observation images by switching the parameter for a first special observation image and the parameter for a second special observation image according to the switching of the first illumination light and the second illumination light.

Second Embodiment

In the first embodiment, the spectral reflectivity of already-known specific biological tissue is used to set specific light amount conditions that allow the signal value of a first blue color signal (first red color signal) for specific biological tissue and the signal value of a second blue color signal (second red color signal) for specific biological tissue to be equal to each other. However, in a second embodiment, image signals, which are obtained in a case where the image of specific biological tissue is picked up during endoscopic diagnosis using an endoscope 12, are used to calculate specific light amount conditions.

Figure 31:
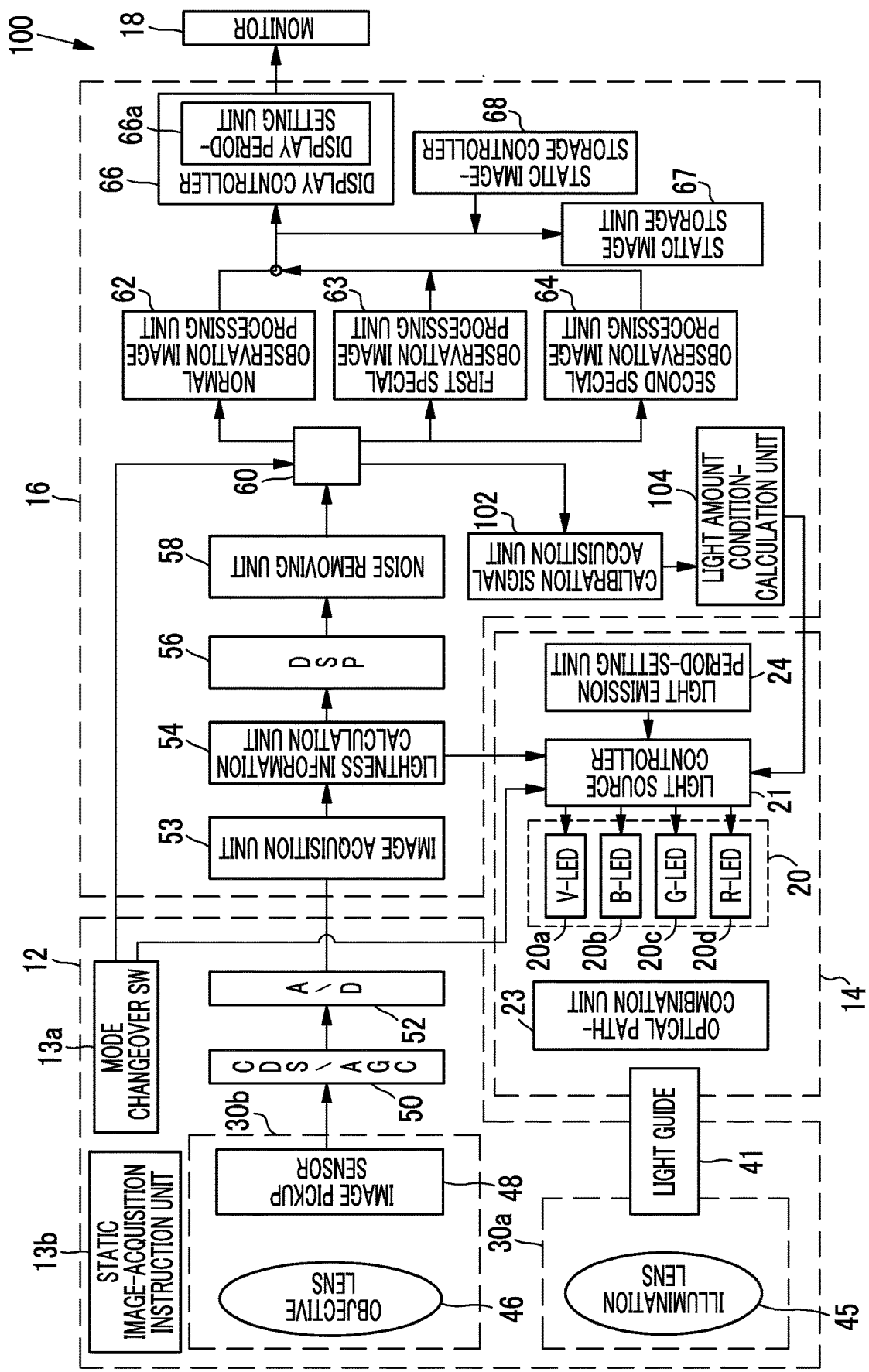
FIG. 31 is a block diagram showing the functions of an endoscope system according to a second embodiment.

In an endoscope system 100 according to the second embodiment, a calibration signal acquisition unit 102 and a light amount condition-calculation unit 104 are provided in a processor device 16 as shown in FIG. 31. Further, a calibration mode used to calculate specific light amount conditions during endoscopic diagnosis is provided in the endoscope system 100, and is switched by a mode changeover SW 13a. Others of the endoscope system 100 are the same as those of the endoscope system 10 according to the first embodiment.

In a case where a user is to calculate specific light amount conditions during endoscopic diagnosis, the user operates the mode changeover SW 13a to switch a mode to the calibration mode in a case where a distal end part 12d of an endoscope reaches specific biological tissue as an object for which specific light amount conditions are to be calculated. In a case where a mode is switched to the calibration mode, different light of the first illumination light and the second illumination light and common light of the first illumination light and the second illumination light are sequentially emitted to the specific biological tissue. Specifically, different light of the first illumination light and the second illumination light are violet light V and blue light B, and common light of the first illumination light and the second illumination light are green light G and red light R. Accordingly, the specific biological tissue is illuminated with violet light V, blue light B, green light G, and red light R sequentially. It is preferable that the specific biological tissue is a part or all of biological tissue of any one of parts, such as the gullet, the stomach, and the large intestine. Further, it is preferable that the specific biological tissue includes at least one of, for example, superficial blood vessels VS1, intermediate blood vessels VS2, or background mucous membrane BM.

Figure 32:
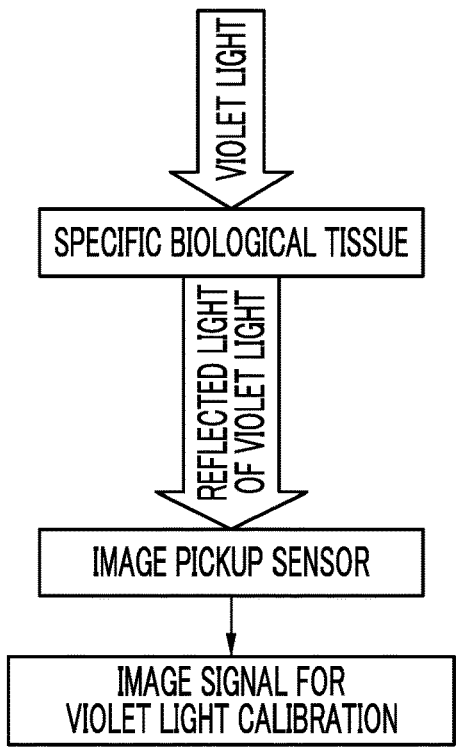
FIG. 32 is a diagram illustrating image signals for violet light calibration.

In a case where the specific biological tissue is illuminated with violet light V as shown in FIG. 32, the reflected light of violet light V from the specific biological tissue is received by the image pickup sensor 48. In this case, image signals for violet light calibration (image signals for first calibration), which are obtained from image pickup using violet light V, is output from the image pickup sensor 48. The image signals for violet light calibration are sent to the processor device 16. The calibration signal acquisition unit 102 acquires the image signals for violet light calibration from the endoscope 12.

Figure 33:
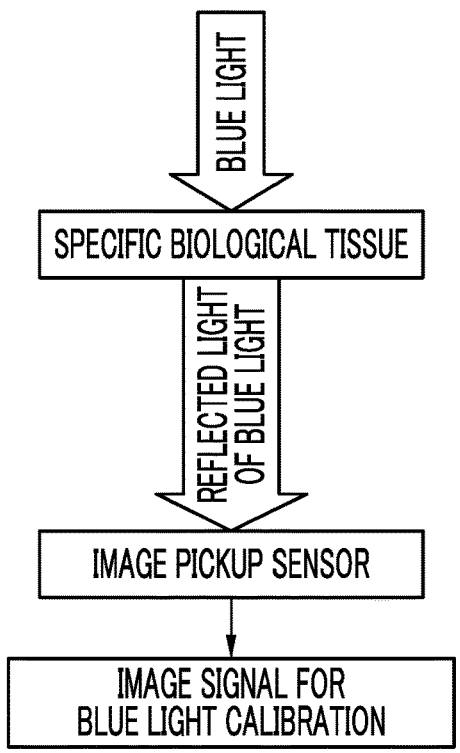
FIG. 33 is a diagram illustrating image signals for blue light calibration.

In a case where the specific biological tissue is illuminated with blue light B as shown in FIG. 33, the reflected light of blue light B from the specific biological tissue is received by the image pickup sensor 48. In this case, image signals for blue light calibration (image signals for first calibration), which are obtained from image pickup using blue light B, is output from the image pickup sensor 48. The image signals for blue light calibration are sent to the processor device 16. The calibration signal acquisition unit 102 acquires the image signals for blue light calibration from the endoscope 12.

Figure 34:
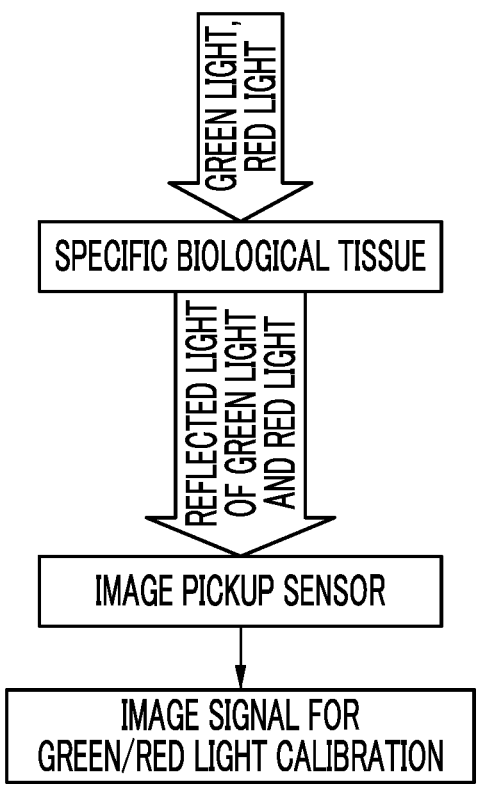
FIG. 34 is a diagram illustrating image signals for green/red light calibration.

In a case where the specific biological tissue is illuminated with green light G and red light R as shown in FIG. 34, the reflected light of green light G and red light R from the specific biological tissue is received by the image pickup sensor 48. In this case, image signals for green/red light calibration (image signals for second calibration), which are obtained from image pickup using green light G and red light R, are output from the image pickup sensor 48. The image signals for green/red light calibration are sent to the processor device 16. The calibration signal acquisition unit 102 acquires the image signals for green/red light calibration from the endoscope 12.

The light amount condition-calculation unit 104 calculates specific light amount conditions of the first illumination light and the second illumination light using the image signals for violet light calibration, the image signals for blue light calibration, and the image signals for green/red light calibration. For example, in a case where violet light V of the first illumination light is emitted with light intensity $\alpha$, blue light B is emitted with light intensity $\beta$, and green light and red light are emitted with light intensity $\gamma$, a blue color signal for violet light calibration (specific color signal for first calibration) output from the B-pixel of the image pickup sensor 48 among the image signals for violet light calibration is denoted by $\alpha CV$. Further, a blue color signal for blue light calibration (specific color signal for first calibration) output from the B-pixel of the image pickup sensor 48 among the image signals for blue light calibration is denoted by $\beta CB$. Furthermore, a blue color signal for green/red light calibration (specific color signal for second calibration) output from the B-pixel of the image pickup sensor 48 among the image signals for green/red light calibration is denoted by $\gamma CGR$.

A first blue color signal B1, which is output from the B-pixel of the image pickup sensor 48 in a case where the first illumination light is emitted, is represented by Equation 3).

$$B1 = \alpha CV + \gamma CGR \qquad \text{Equation 3)}$$

Further, a second blue color signal B2, which is output from the B-pixel of the image pickup sensor 48 in a case where the second illumination light is emitted, is represented by Equation 4).

$$B2 = \beta CB + \gamma CGR \qquad \text{Equation 4)}$$

Here, in a case where $\alpha CV$ is set to, for example, "100", $\beta CB$ is set to, for example, "50", and $\gamma CGR$ is set to, for example, "20", Equation 3) is transformed into Equation 3').

$$B1 = \alpha CV / \beta CB \times \beta CB + \gamma CGR \qquad \text{Equation 3')}$$

Since $\alpha CV / \beta CB$ is "2", Equation 3') is as follows.

$$B1 = 2 \times \beta CB + \gamma CGR \qquad \text{Equation 3')}$$

In order to make Equation 3') and Equation 4) be equal to each other, it is necessary to multiply the first term of Equation 4) by "2". From the above description, the light amount condition-calculation unit 104 sets the light intensity ratios Vs1:Bs1:Gs1:Rs1, which are the light amount condition of the first illumination light, to "α:0: δ:ε", sets the light intensity ratios Vs2:Bs2:Gs2:Rs2, which are the light amount condition of the second illumination light, to "0:2×β:δ:ε", and calculates specific light amount conditions. "δ" denotes the light intensity of green light G included in the first illumination light or the second illumination light, and "ε" denotes the light intensity of red light R included in the first illumination light or the second illumination light.

The hardware structures of the processing units included in the processor device 16 in the first and second embodiments, such as the image acquisition unit 53, the lightness information calculation unit 54, the DSP 56, the noise removing unit 58, the normal observation image processing unit 62, the first special observation image processing unit 63, the second special observation image processing unit 64, the static image storage unit 67, the display controller 66, the display period-setting unit 66a, the static image-storage controller 68, the specific image processing unit 90, the calibration signal acquisition unit 102, and the light amount condition-calculation unit 104, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a graphical processing unit (GPU); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, a combination of a CPU and an FPGA, or a combination of a CPU and a GPU). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

The invention can be applied to various medical image processing devices other than the processor device that is to be combined with the endoscope systems described in the first and second embodiments.

EXPLANATION OF REFERENCES

10: endoscope system
12: endoscope
12a: insertion part
12b: operation part
12c: bendable part
12d: distal end part
12e: angle knob
13b: static image-acquisition instruction unit
14: light source device
16: processor device
18: monitor
19: user interface
20: light source unit
20a: violet light emitting diode (V-LED)
20b: blue light emitting diode (B-LED)
20c: green light emitting diode (G-LED)
20d: red light emitting diode (R-LED)
21: light source controller
23: optical path-combination unit
24: light emission period-setting unit
26a: slide bar
26b: slide bar
27a: slider
27b: slider
30a: illumination optical system
30b: image pickup optical system
41: light guide
45: illumination lens
46: objective lens
48: image pickup sensor
48b: B-filter
48g: G-filter
48r: R-filter
50: CDS/AGC circuit
53: image acquisition unit
54: lightness information calculation unit
56: digital signal processor (DSP)
58: noise removing unit
60: signal switching unit
62: normal observation image processing unit
63: first special observation image processing unit
64: second special observation image processing unit
66: display controller
66a: display period-setting unit
67: static image storage unit
68: static image-storage controller
70: graph
71: graph
74: high-oxygen portion
76: high-oxygen portion
78: low-oxygen portion
80: low-oxygen portion
84a: slide bar
84b: slide bar
86a: slider
86b: slider
90: specific image processing unit
100: endoscope system
102: calibration signal acquisition unit
104: light amount condition-calculation unit
SP1: first special observation image
SP2: second special observation image
VP: violet light image
GRP: green-red light image
VS1: superficial blood vessel
VS2: intermediate blood vessel
BM: background mucous membrane

What is claimed is:

1. An endoscope system comprising:
a light source that emits first illumination light and second illumination light having an emission spectrum different from an emission spectrum of the first illumination light;
a light source controller that automatically switches the first illumination light and the second illumination light and emits each of the first illumination light and the second illumination light for a light emission period of at least one or more frames;
an image pickup sensor that includes specific pixels having sensitivity to the first illumination light and the second illumination light; and
a processor configured to function as:
   an image acquisition unit that acquires first image signals obtained in a case where an image of biological tissue illuminated with the first illumination light is picked up by the image pickup sensor, and second image signals obtained in a case where an image of biological tissue illuminated with the second illumination light is picked up by the image pickup sensor; and
   a display controller that causes a display to automatically switch and display a first observation image obtained on the basis of the first image signals and a second observation image obtained on the basis of the second image signals,
wherein the first image signals include first specific color signals output from the specific pixels, and the second image signals include second specific color signals output from the specific pixels,
the light source controller causes the first illumination light and the second illumination light to be emitted under specific light amount conditions, so that a signal value of the first specific color signal for specific biological tissue corresponding to at least specific biological tissue, which is a part of the biological tissue, among the first specific color signals is equal to a signal value of the second specific color signal for specific biological tissue corresponding to at least the specific biological tissue among the second specific color signals,
a light amount condition of the first illumination light and a light amount condition of the second illumination light in a case where a first calculation value obtained using a light intensity of the first illumination light, a spectral reflectivity of the specific biological tissue, and a spectral sensitivity of the specific pixel is equal to a second calculation value obtained using a light intensity of the second illumination light, the spectral reflectivity of the specific biological tissue, and the spectral sensitivity of the specific pixel are used as the specific light amount conditions,
the spectral reflectivity of the specific biological tissue is an average spectral reflectivity of a plurality of parts obtained by averaging of spectral reflectivities of biological tissue of the plurality of parts,
the plurality of parts include a gullet, a stomach, and a large intestine.

2. An endoscope system comprising:
a light source that emits first illumination light and second illumination light having an emission spectrum different from an emission spectrum of the first illumination light;
a light source controller that automatically switches the first illumination light and the second illumination light and emits each of the first illumination light and the second illumination light for a light emission period of at least one or more frames;
an image pickup sensor that includes specific pixels having sensitivity to the first illumination light and the second illumination light; and
a processor configured to function as:
   an image acquisition unit that acquires first image signals obtained in a case where an image of biological tissue illuminated with the first illumination light is picked up by the image pickup sensor, and second image signals obtained in a case where an image of biological tissue illuminated with the second illumination light is picked up by the image pickup sensor; and
   a display controller that causes a display to automatically switch and display a first observation image obtained on the basis of the first image signals and a second observation image obtained on the basis of the second image signals,
wherein the first image signals include first specific color signals output from the specific pixels, and the second image signals include second specific color signals output from the specific pixels,
the light source controller causes the first illumination light and the second illumination light to be emitted under specific light amount conditions, so that a signal value of the first specific color signal for specific biological tissue corresponding to at least specific biological tissue, which is a part of the biological tissue, among the first specific color signals is equal to a signal value of the second specific color signal for specific biological tissue corresponding to at least the specific biological tissue among the second specific color signals,
a light amount condition of the first illumination light and a light amount condition of the second illumination light in a case where a first calculation value obtained using a light intensity of the first illumination light, a spectral reflectivity of the specific biological tissue, and a spectral sensitivity of the specific pixel is equal to a second calculation value obtained using a light intensity of the second illumination light, the spectral reflectivity of the specific biological tissue, and the spectral sensitivity of the specific pixel are used as the specific light amount conditions, and
the spectral reflectivity of the specific biological tissue is any one of a spectral reflectivity of a high-oxygen portion including a specific percentage or higher of oxyhemoglobin or a spectral reflectivity of a low-oxygen portion including a specific percentage or higher of reduced hemoglobin.

3. The endoscope system according to claim 1, wherein the processor is further configured to function as:
a calibration signal acquisition unit that acquires image signals for first calibration obtained in a case where an image of the specific biological tissue illuminated with different light of the first illumination light and the second illumination light is picked up by the image pickup sensor and image signals for second calibration obtained in a case where an image of the specific biological tissue illuminated with common light of the first illumination light and the second illumination light is picked up by the image pickup sensor; and
a light amount condition-calculation unit that calculates the specific light amount conditions using a specific color signal for first calibration output from the specific pixel among the image signals for first calibration and a specific color signal for second calibration output from the specific pixel among the image signals for second calibration.

4. An endoscope system comprising:
a light source that emits first illumination light and second illumination light having an emission spectrum different from an emission spectrum of the first illumination light;
a light source controller that automatically switches the first illumination light and the second illumination light and emits each of the first illumination light and the second illumination light for a light emission period of at least one or more frames;
an image pickup sensor that includes specific pixels having sensitivity to the first illumination light and the second illumination light; and
a processor configured to function as:
   an image acquisition unit that acquires first image signals obtained in a case where an image of biological tissue illuminated with the first illumination light is picked up by the image pickup sensor, and second image signals obtained in a case where an image of biological tissue illuminated with the second illumination light is picked up by the image pickup sensor,
wherein the first illumination light includes violet light, green light, and red light and the second illumination light includes blue light, green light, and red light,
   the first image signals include first specific color signals output from the specific pixels, and the second image signals include second specific color signals output from the specific pixels, and
the light source controller causes the first illumination light and the second illumination light to be emitted under specific light amount conditions, so that a signal value of the first specific color signal for specific biological tissue corresponding to at least specific biological tissue, which is a part of the biological tissue, among the first specific color signals is equal to a signal value of the second specific color signal for specific biological tissue corresponding to at least the specific biological tissue among the second specific color signals.

5. The endoscope system according to claim 4,
wherein light intensity ratios of the green light and the red light included in the first illumination light are equal to light intensity ratios of the green light and the red light included in the second illumination light, and
the specific pixel is a blue pixel having sensitivity to the violet light and the blue light.

6. The endoscope system according to claim 4,
wherein a light intensity ratio of the violet light included in the first illumination light is higher than a light intensity ratio of the blue light included in the first illumination light,
a light intensity ratio of the blue light included in the second illumination light is higher than a light intensity ratio of the violet light included in the second illumination light,
light intensity ratios of the green light and the red light included in the first illumination light are equal to light intensity ratios of the green light and the red light included in the second illumination light,
the light intensity ratio of the violet light included in the first illumination light is different from the light intensity ratio of the violet light included in the second illumination light, and the light intensity ratio of the blue light included in the first illumination light is different from the light intensity ratio of the blue light included in the second illumination light, and
the specific pixel is a blue pixel having sensitivity to the violet light and the blue light.

7. The endoscope system according to claim 4,
wherein the first illumination light includes first red narrow-band light and the second illumination light includes second red narrow-band light of which a wavelength is different from a wavelength of the first red narrow-band light, and
the specific pixel is a red pixel having sensitivity to the first red narrow-band light and the second red narrow-band light.

8. The endoscope system according to claim 4,
wherein a light amount condition of the first illumination light and a light amount condition of the second illumination light in a case where a first calculation value obtained using a light intensity of the first illumination light, a spectral reflectivity of the specific biological tissue, and a spectral sensitivity of the specific pixel is equal to a second calculation value obtained using a light intensity of the second illumination light, the spectral reflectivity of the specific biological tissue, and the spectral sensitivity of the specific pixel are used as the specific light amount conditions.

9. The endoscope system according to claim 8,
wherein the spectral reflectivity of the specific biological tissue is an average spectral reflectivity of a plurality of parts obtained by averaging of spectral reflectivities of biological tissue of the plurality of parts.

10. The endoscope system according to claim 9,
wherein the plurality of parts include a gullet, a stomach, and a large intestine.

11. The endoscope system according to claim 8,
wherein the spectral reflectivity of the specific biological tissue is a spectral reflectivity of a background mucous membrane.

12. The endoscope system according to claim 8,
wherein the spectral reflectivity of the specific biological tissue is an average spectral reflectivity of the entire biological tissue.

13. The endoscope system according to claim 8,
wherein the spectral reflectivity of the specific biological tissue is any one of a spectral reflectivity of a high-oxygen portion including a specific percentage or higher of oxyhemoglobin or a spectral reflectivity of a low-oxygen portion including a specific percentage or higher of reduced hemoglobin.

14. The endoscope system according to claim 4, wherein the processor is further configured to function as:
a calibration signal acquisition unit that acquires image signals for first calibration obtained in a case where an image of the specific biological tissue illuminated with different light of the first illumination light and the second illumination light is picked up by the image pickup sensor and image signals for second calibration obtained in a case where an image of the specific biological tissue illuminated with common light of the first illumination light and the second illumination light is picked up by the image pickup sensor; and
a light amount condition-calculation unit that calculates the specific light amount conditions using a specific color signal for first calibration output from the specific pixel among the image signals for first calibration and a specific color signal for second calibration output from the specific pixel among the image signals for second calibration.

\* \* \* \* \*